United States Patent [19]
Kuestner et al.

[11] Patent Number: 6,008,322
[45] Date of Patent: Dec. 28, 1999

[54] STANNIOCALCIN-2

[75] Inventors: Rolf E. Kuestner, Bothell; Darrell C. Conklin; Si Lok, both of Seattle, all of Wash.; Michele Buddle, Poughkeepsie, N.Y.; William Downey, Seattle, Wash.

[73] Assignee: ZymoGenetics, Inc., Seattle, Wash.

[21] Appl. No.: 08/831,132

[22] Filed: Apr. 1, 1997

[51] Int. Cl.$^6$ .................................................. C07K 14/47
[52] U.S. Cl. ........................... 530/350; 530/397; 530/395
[58] Field of Search ..................................... 530/350, 397, 530/395

[56] References Cited

U.S. PATENT DOCUMENTS 5,837,498  11/1998  Olsen et al. ............................ 435/69.4

FOREIGN PATENT DOCUMENTS

| WO88/0394 | 6/1988 | WIPO . |
| WO95/24411 | 9/1994 | WIPO . |
| WO96/15147 | 5/1996 | WIPO . |

OTHER PUBLICATIONS

Ngo et al, in:The protein folding problem and tertiary structure prediction, Merz et al.(ed), Birkhauser, Boston, MA, pp. 492–495, 1994.

INC260632, Lifeseq™ Clone Information Results, Incyte Pharmaceuticals, Inc., 1995.

INC2484355, Lifeseq™ Clone Information Results, Incyte Pharmaceuticals, Inc., 1997.

INC2474784, Lifeseq™ Clone Information Results, Incyte Pharmaceuticals, Inc., 1997.

INC2474827, Lifeseq™ Clone Information Results, Incyte Pharmaceuticals, Inc., 1997.

INC2479915, Lifeseq™ Clone Information Results, Incyte Pharmaceuticals, Inc., 1997.

Genbank Acc, No. H98195, Hillier et al., WashU–Merck EST Project, 1995.

Genbank Acc. No. AA195455, Hillier et al., WashU–Merck EST Project, 1995.

Genbank Acc. No. AA223369, Hillier et al., WashU–Merck EST Project, 1995.

HNT2RAT01, Lifeseq™ Library Information Results, Incyte Pharmaceuticals, Inc., date unknown.

SMCANOT01, Lifeseq™ Library Information Results, Incyte Pharmaceuticals, Inc., date unknown.

Wagner et al., Molecular and Cellular Endocrinology 90:7–15, 1992.

*Primary Examiner*—Lorraine Spector
*Assistant Examiner*—Eliane Lazar-Wesley
*Attorney, Agent, or Firm*—Deborah A. Sawislak

[57] ABSTRACT

The present invention relates to polynucleotide and polypeptide molecules for stanniocalcin-2, a novel member of the stanniocalcin family. The polypeptides, and polynucleotides encoding them, modulate electrolyte homeostasis. The present invention also includes antibodies to the stanniocalcin-2 polypeptides.

8 Claims, 1 Drawing Sheet

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 906 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: sig_peptide
      (B) LOCATION: 1..72

(ix) FEATURE:
      (A) NAME/KEY: mat_peptide 6,008,322

31

32

-continued (B) LOCATION: 73..906

(ix) FEATURE:
    (A) NAME/KEY: CDS
    (B) LOCATION: 1..906

(xi) SEQUENCE DESCRIPTION: SEQ ID NO:1:

```
ATG TGT GCC GAG CGG CTG GGC CAG TTC ATG ACC CTG GCT TTG GTG TTG        48
Met Cys Ala Glu Arg Leu Gly Gln Phe Met Thr Leu Ala Leu Val Leu
-24             -20                 -15                 -10

GCC ACC TTT GAC CCG GCG CGG GGG ACC GAC GCC ACC AAC CCA CCC GAG        96
Ala Thr Phe Asp Pro Ala Arg Gly Thr Asp Ala Thr Asn Pro Pro Glu
             -5                   1                   5

GGT CCC CAA GAC AGG AGC TCC CAG CAG AAA GGC CGC CTG TCC CTG CAG       144
Gly Pro Gln Asp Arg Ser Ser Gln Gln Lys Gly Arg Leu Ser Leu Gln
         10                  15                  20

AAT ACA GCG GAG ATC CAG CAC TGT TTG GTC AAC GCT GGC GAT GTG GGG       192
Asn Thr Ala Glu Ile Gln His Cys Leu Val Asn Ala Gly Asp Val Gly
 25                  30                  35                  40

TGT GGC GTG TTT GAA TGT TTC GAG AAC AAC TCT TGT GAG ATT CGG GGC       240
Cys Gly Val Phe Glu Cys Phe Glu Asn Asn Ser Cys Glu Ile Arg Gly
                 45                  50                  55

TTA CAT GGG ATT TGC ATG ACT TTT CTG CAC AAC GCT GGA AAA TTT GAT       288
Leu His Gly Ile Cys Met Thr Phe Leu His Asn Ala Gly Lys Phe Asp
             60                  65                  70

GCC CAG GGC AAG TCA TTC ATC AAA GAC GCC TTG AAA TGT AAG GCC CAC       336
Ala Gln Gly Lys Ser Phe Ile Lys Asp Ala Leu Lys Cys Lys Ala His
         75                  80                  85

GCT CTG CGG CAC AGG TTC GGC TGC ATA AGC CGG AAG TGC CCG GCC ATC       384
Ala Leu Arg His Arg Phe Gly Cys Ile Ser Arg Lys Cys Pro Ala Ile
     90                  95                 100

AGG GAA ATG GTG TCC CAG TTG CAG CGG GAA TGC TAC CTC AAG CAC GAC       432
Arg Glu Met Val Ser Gln Leu Gln Arg Glu Cys Tyr Leu Lys His Asp
105                 110                 115                 120

CTG TGC GCG GCT GCC CAG GAG AAC ACC CGG GTG ATA GTG GAG ATG ATC       480
Leu Cys Ala Ala Ala Gln Glu Asn Thr Arg Val Ile Val Glu Met Ile
                125                 130                 135

CAT TTC AAG GAC TTG CTG CTG CAC GAA CCC TAC GTG GAC CTC GTG AAC       528
His Phe Lys Asp Leu Leu Leu His Glu Pro Tyr Val Asp Leu Val Asn
            140                 145                 150

TTG CTG CTG ACC TGT GGG GAG GAG GTG AAG GAG GCC ATC ACC CAC AGC       576
Leu Leu Leu Thr Cys Gly Glu Glu Val Lys Glu Ala Ile Thr His Ser
        155                 160                 165

GTG CAG GTT CAG TGT GAG CAG AAC TGG GGA AGC CTG TGC TCC ATC TTG       624
Val Gln Val Gln Cys Glu Gln Asn Trp Gly Ser Leu Cys Ser Ile Leu
    170                 175                 180

AGC TTC TGC ACC TCG GCC ATC CAG AAG CCT CCC ACG GCG CCC CCC GAG       672
Ser Phe Cys Thr Ser Ala Ile Gln Lys Pro Pro Thr Ala Pro Pro Glu
185                 190                 195                 200

CGC CAG CCC CAG GTG GAC AGA ACC AAG CTC TCC AGG GCC CAC CAC GGG       720
Arg Gln Pro Gln Val Asp Arg Thr Lys Leu Ser Arg Ala His His Gly
                205                 210                 215

GAA GCA GGA CAT CAC CTC CCA GAG CCC AGC AGT AGG GAG ACT GGC CGA       768
Glu Ala Gly His His Leu Pro Glu Pro Ser Ser Arg Glu Thr Gly Arg
            220                 225                 230

GGT GCC AAG GGT GAG CGA GGT AGC AAG AGC CAC CCA AAC GCC CAT GCC       816
Gly Ala Lys Gly Glu Arg Gly Ser Lys Ser His Pro Asn Ala His Ala
        235                 240                 245

CGA GGC AGA GTC GGG GGC CTT GGG GCT CAG GGA CCT TCC GGA AGC AGC       864
Arg Gly Arg Val Gly Gly Leu Gly Ala Gln Gly Pro Ser Gly Ser Ser
    250                 255                 260
```

```
GAG TGG GAA GAC GAA CAG TCT GAG TAT TCT GAT ATC CGG AGG         906
Glu Trp Glu Asp Glu Gln Ser Glu Tyr Ser Asp Ile Arg Arg
265             270                 275
```

(2) INFORMATION FOR SEQ ID NO:2:

(i) SEQUENCE CHARACTERISTICS:
        (A) LENGTH: 302 amino acids
        (B) TYPE: amino acid
        (D) TOPOLOGY: linear (ii) MOLECULE TYPE: protein (xi) SEQUENCE DESCRIPTION: SEQ ID NO:2:

```
Met Cys Ala Glu Arg Leu Gly Gln Phe Met Thr Leu Ala Leu Val Leu
-24             -20                 -15                 -10

Ala Thr Phe Asp Pro Ala Arg Gly Thr Asp Ala Thr Asn Pro Pro Glu
            -5                  1                   5

Gly Pro Gln Asp Arg Ser Ser Gln Gln Lys Gly Arg Leu Ser Leu Gln
        10                  15                  20

Asn Thr Ala Glu Ile Gln His Cys Leu Val Asn Ala Gly Asp Val Gly
25                  30                  35                  40

Cys Gly Val Phe Glu Cys Phe Glu Asn Asn Ser Cys Glu Ile Arg Gly
                45                  50                  55

Leu His Gly Ile Cys Met Thr Phe Leu His Asn Ala Gly Lys Phe Asp
            60                  65                  70

Ala Gln Gly Lys Ser Phe Ile Lys Asp Ala Leu Lys Cys Lys Ala His
        75                  80                  85

Ala Leu Arg His Arg Phe Gly Cys Ile Ser Arg Lys Cys Pro Ala Ile
    90                  95                  100

Arg Glu Met Val Ser Gln Leu Gln Arg Glu Cys Tyr Leu Lys His Asp
105                 110                 115                 120

Leu Cys Ala Ala Ala Gln Glu Asn Thr Arg Val Ile Val Glu Met Ile
                125                 130                 135

His Phe Lys Asp Leu Leu Leu His Glu Pro Tyr Val Asp Leu Val Asn
            140                 145                 150

Leu Leu Leu Thr Cys Gly Glu Glu Val Lys Glu Ala Ile Thr His Ser
        155                 160                 165

Val Gln Val Gln Cys Glu Gln Asn Trp Gly Ser Leu Cys Ser Ile Leu
    170                 175                 180

Ser Phe Cys Thr Ser Ala Ile Gln Lys Pro Pro Thr Ala Pro Pro Glu
185                 190                 195                 200

Arg Gln Pro Gln Val Asp Arg Thr Lys Leu Ser Arg Ala His His Gly
                205                 210                 215

Glu Ala Gly His His Leu Pro Glu Pro Ser Ser Arg Glu Thr Gly Arg
            220                 225                 230

Gly Ala Lys Gly Glu Arg Gly Ser Lys Ser His Pro Asn Ala His Ala
        235                 240                 245

Arg Gly Arg Val Gly Gly Leu Gly Ala Gln Gly Pro Ser Gly Ser Ser
    250                 255                 260

Glu Trp Glu Asp Glu Gln Ser Glu Tyr Ser Asp Ile Arg Arg
265                 270                 275
```

(2) INFORMATION FOR SEQ ID NO:3:

(i) SEQUENCE CHARACTERISTICS:
        (A) LENGTH: 30 amino acids
        (B) TYPE: amino acid
        (C) STRANDEDNESS: single (D) TOPOLOGY: linear (xi) SEQUENCE DESCRIPTION: SEQ ID NO:3:

Thr Asp Ala Thr Asn Pro Pro Glu Gly Pro Gln Asp Arg Gly Ser Gln
1               5                   10                  15

Gln Lys Gly Arg Leu Ser Leu Gln Asn Thr Ala Glu Ile Gln
            20                  25                  30

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (vii) IMMEDIATE SOURCE:
        (B) CLONE: ZC10189

(xi) SEQUENCE DESCRIPTION: SEQ ID NO:4:

CCTGCAGAAT ACAGCGGAGG ATC                                                  23

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (vii) IMMEDIATE SOURCE:
        (B) CLONE: ZC10191

(xi) SEQUENCE DESCRIPTION: SEQ ID NO:5:

CCGCAGAGCG TGGGCCTTAC ATT                                                  23

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (vii) IMMEDIATE SOURCE:
        (B) CLONE: ZC694

(xi) SEQUENCE DESCRIPTION: SEQ ID NO:6:

TAATACGACT CACTATAGGG                                                        20

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (vii) IMMEDIATE SOURCE:
        (B) CLONE: ZC695

(xi) SEQUENCE DESCRIPTION: SEQ ID NO:7:

GATTTAGGTG ACACTATAG                                                         19

(2) INFORMATION FOR SEQ ID NO:8:

(i) SEQUENCE CHARACTERISTICS:
        (A) LENGTH: 29 base pairs
        (B) TYPE: nucleic acid

```
              (C) STRANDEDNESS: single
              (D) TOPOLOGY: linear (vii) IMMEDIATE SOURCE:
              (B) CLONE: ZC10139

(xi) SEQUENCE DESCRIPTION: SEQ ID NO:8:

AGCGGAGGAT CCAGCATGTT TGGTCAACG                                        29

(2) INFORMATION FOR SEQ ID NO:9:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (vii) IMMEDIATE SOURCE:
              (B) CLONE: ZC10130

(xi) SEQUENCE DESCRIPTION: SEQ ID NO:9:

AGAAAGGCCG CCTGTCCCTG CAGAATAC                                         28

(2) INFORMATION FOR SEQ ID NO:10:

(i) SEQUENCE CHARACTERISTICS:
              (A) LENGTH: 34 base pairs
              (B) TYPE: nucleic acid
              (C) STRANDEDNESS: single
              (D) TOPOLOGY: linear (vii) IMMEDIATE SOURCE:
              (B) CLONE: ZC10772

(xi) SEQUENCE DESCRIPTION: SEQ ID NO:10:

GATATCGGAT CCTGGGCCAG TTCATGACCC TGGC                                  34

(2) INFORMATION FOR SEQ ID NO:11:

(i) SEQUENCE CHARACTERISTICS:
              (A) LENGTH: 32 base pairs
              (B) TYPE: nucleic acid
              (C) STRANDEDNESS: single
              (D) TOPOLOGY: linear (vii) IMMEDIATE SOURCE:
              (B) CLONE: ZC10773

(xi) SEQUENCE DESCRIPTION: SEQ ID NO:11:

TACGGAGAAT TCGGAATGTC CATAGATAAG AA                                    32

(2) INFORMATION FOR SEQ ID NO:12:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (vii) IMMEDIATE SOURCE:
              (B) CLONE: ZC10140

(xi) SEQUENCE DESCRIPTION: SEQ ID NO:12:

GTCATGCAAA TCCCATGTAA GCCCCGAA                                         28

(2) INFORMATION FOR SEQ ID NO:13:

(i) SEQUENCE CHARACTERISTICS:
              (A) LENGTH: 888 base pairs
              (B) TYPE: nucleic acid
```

(C) STRANDEDNESS: single
(D) TOPOLOGY: linear (ii) MOLECULE TYPE: cDNA (ix) FEATURE:
    (A) NAME/KEY: sig_peptide
    (B) LOCATION: 1..72

(ix) FEATURE:
    (A) NAME/KEY: mat_peptide
    (B) LOCATION: 73..888

(ix) FEATURE:
    (A) NAME/KEY: CDS
    (B) LOCATION: 1..888

(xi) SEQUENCE DESCRIPTION: SEQ ID NO:13:

| | | | | | | | | | | | | | | | | |
|---|---|---|---|---|---|---|---|---|---|---|---|---|---|---|---|---|
| ATG | TGT | GCG | GAG | CGG | CTG | GGC | CAG | TTT | GTG | ACC | CTG | GCT | TTG | GTG | TTT | 48 |
| Met | Cys | Ala | Glu | Arg | Leu | Gly | Gln | Phe | Val | Thr | Leu | Ala | Leu | Val | Phe | |
| -24 | | | -20 | | | | -15 | | | | | -10 | | | | |

| GCC | ACC | TTG | GAC | CCG | GCG | CAG | GGG | ACG | GAC | TCC | ACG | AAC | CCT | CCG | GAA | 96 |
|---|---|---|---|---|---|---|---|---|---|---|---|---|---|---|---|---|
| Ala | Thr | Leu | Asp | Pro | Ala | Gln | Gly | Thr | Asp | Ser | Thr | Asn | Pro | Pro | Glu | |
| | | | -5 | | | | 1 | | | | 5 | | | | | |

| GGT | CCC | CAA | GAC | AGG | AGC | TCG | CAG | CAG | AAA | GGC | CGT | CTG | TCC | CTG | CAG | 144 |
|---|---|---|---|---|---|---|---|---|---|---|---|---|---|---|---|---|
| Gly | Pro | Gln | Asp | Arg | Ser | Ser | Gln | Gln | Lys | Gly | Arg | Leu | Ser | Leu | Gln | |
| | 10 | | | | 15 | | | | | 20 | | | | | | |

| AAC | ACA | GCG | GAG | ATC | CAG | CAC | TGT | TTG | GTC | AAT | GCC | GGG | GAC | GTG | GGC | 192 |
|---|---|---|---|---|---|---|---|---|---|---|---|---|---|---|---|---|
| Asn | Thr | Ala | Glu | Ile | Gln | His | Cys | Leu | Val | Asn | Ala | Gly | Asp | Val | Gly | |
| 25 | | | | | 30 | | | | | 35 | | | | | 40 | |

| TGT | GGT | GTG | TTT | GAG | TGT | TTC | GAG | AAC | AAC | TCT | TGT | GAA | ATC | CAG | GGT | 240 |
|---|---|---|---|---|---|---|---|---|---|---|---|---|---|---|---|---|
| Cys | Gly | Val | Phe | Glu | Cys | Phe | Glu | Asn | Asn | Ser | Cys | Glu | Ile | Gln | Gly | |
| | | | | 45 | | | | | 50 | | | | | 55 | | |

| TTA | CAT | GGG | ATT | TGC | ATG | ACG | TTT | CTG | CAC | AAC | GCT | GGA | AAA | TTC | GAT | 288 |
|---|---|---|---|---|---|---|---|---|---|---|---|---|---|---|---|---|
| Leu | His | Gly | Ile | Cys | Met | Thr | Phe | Leu | His | Asn | Ala | Gly | Lys | Phe | Asp | |
| | | | 60 | | | | | 65 | | | | | 70 | | | |

| GCC | CAG | GGA | AAG | TCA | TTC | ATC | AAG | GAT | GCC | CTG | AGG | TGC | AAG | GCC | CAT | 336 |
|---|---|---|---|---|---|---|---|---|---|---|---|---|---|---|---|---|
| Ala | Gln | Gly | Lys | Ser | Phe | Ile | Lys | Asp | Ala | Leu | Arg | Cys | Lys | Ala | His | |
| | | 75 | | | | | 80 | | | | | 85 | | | | |

| GCC | CTG | CGT | CAT | AAA | TTT | GGC | TGC | ATC | AGC | AGG | AAG | TGT | CCA | GCA | ATT | 384 |
|---|---|---|---|---|---|---|---|---|---|---|---|---|---|---|---|---|
| Ala | Leu | Arg | His | Lys | Phe | Gly | Cys | Ile | Ser | Arg | Lys | Cys | Pro | Ala | Ile | |
| | 90 | | | | | 95 | | | | | 100 | | | | | |

| AGG | GAA | ATG | GTT | TTC | CAG | TTG | CAG | AGG | GAA | TGC | TAT | CTG | AAG | CAT | GAC | 432 |
|---|---|---|---|---|---|---|---|---|---|---|---|---|---|---|---|---|
| Arg | Glu | Met | Val | Phe | Gln | Leu | Gln | Arg | Glu | Cys | Tyr | Leu | Lys | His | Asp | |
| 105 | | | | | 110 | | | | | 115 | | | | | 120 | |

| CTG | TGC | TCC | GCA | GCC | CAG | GAG | AAC | GTC | GGT | GTG | ATT | GTG | GAG | ATG | ATT | 480 |
|---|---|---|---|---|---|---|---|---|---|---|---|---|---|---|---|---|
| Leu | Cys | Ser | Ala | Ala | Gln | Glu | Asn | Val | Gly | Val | Ile | Val | Glu | Met | Ile | |
| | | | | 125 | | | | | 130 | | | | | 135 | | |

| CAT | TTC | AAG | GAT | CTC | CTG | CTG | CAT | GAG | CCC | TAT | GTG | GAC | CTT | GTG | AAC | 528 |
|---|---|---|---|---|---|---|---|---|---|---|---|---|---|---|---|---|
| His | Phe | Lys | Asp | Leu | Leu | Leu | His | Glu | Pro | Tyr | Val | Asp | Leu | Val | Asn | |
| | | | 140 | | | | | 145 | | | | | 150 | | | |

| CTG | CTG | CTG | ACC | TGC | GGG | GAA | GAT | GTG | AAG | GAG | GCA | GTC | ACC | CGC | AGC | 576 |
|---|---|---|---|---|---|---|---|---|---|---|---|---|---|---|---|---|
| Leu | Leu | Leu | Thr | Cys | Gly | Glu | Asp | Val | Lys | Glu | Ala | Val | Thr | Arg | Ser | |
| | | 155 | | | | | 160 | | | | | 165 | | | | |

| GTC | CAG | GCT | CAG | TGT | GAA | CAG | AGC | TGG | GGA | GGC | CTC | TGC | TCC | ATC | CTG | 624 |
|---|---|---|---|---|---|---|---|---|---|---|---|---|---|---|---|---|
| Val | Gln | Ala | Gln | Cys | Glu | Gln | Ser | Trp | Gly | Gly | Leu | Cys | Ser | Ile | Leu | |
| | 170 | | | | | 175 | | | | | 180 | | | | | |

| AGT | TTC | TGC | ACC | TCC | AAT | ATA | CAG | AGA | CCT | CCC | ACG | GCA | GCC | CCA | GAG | 672 |
|---|---|---|---|---|---|---|---|---|---|---|---|---|---|---|---|---|
| Ser | Phe | Cys | Thr | Ser | Asn | Ile | Gln | Arg | Pro | Pro | Thr | Ala | Ala | Pro | Glu | |
| 185 | | | | | 190 | | | | | 195 | | | | | 200 | |

| CAT | CAG | CCC | CTG | GCA | GAC | AGG | GCT | CAG | CTC | TCC | AGG | CCT | CAC | CAC | CGG | 720 |
|---|---|---|---|---|---|---|---|---|---|---|---|---|---|---|---|---|
| His | Gln | Pro | Leu | Ala | Asp | Arg | Ala | Gln | Leu | Ser | Arg | Pro | His | His | Arg | |
| | | | | 205 | | | | | 210 | | | | | 215 | | |

| GAC | ACA | GAC | CAT | CAC | CTA | ACA | GCC | AAC | AGA | GGT | GCC | AAG | GGT | GAG | CGA | 768 |

```
Asp Thr Asp His His Leu Thr Ala Asn Arg Gly Ala Lys Gly Glu Arg
        220                 225                 230

GGG AGC AAA AGC CAC CCG AAT GCC CAT GCT CGA GGC AGA ACC GGT GGC        816
Gly Ser Lys Ser His Pro Asn Ala His Ala Arg Gly Arg Thr Gly Gly
        235                 240                 245

CAG AGC GCT CAG GGA CCC TCT GGA AGC AGT GAG TGG GAG GAT GAA CAG        864
Gln Ser Ala Gln Gly Pro Ser Gly Ser Ser Glu Trp Glu Asp Glu Gln
    250                 255                 260

TCT GAG TAT TCC GAC ATC CGG AGG                                        888
Ser Glu Tyr Ser Asp Ile Arg Arg
265                 270

(2) INFORMATION FOR SEQ ID NO:14:

(i) SEQUENCE CHARACTERISTICS:
        (A) LENGTH: 296 amino acids
        (B) TYPE: amino acid
        (D) TOPOLOGY: linear (ii) MOLECULE TYPE: protein (xi) SEQUENCE DESCRIPTION: SEQ ID NO:14:

Met Cys Ala Glu Arg Leu Gly Gln Phe Val Thr Leu Ala Leu Val Phe
-24             -20                 -15                 -10

Ala Thr Leu Asp Pro Ala Gln Gly Thr Asp Ser Thr Asn Pro Pro Glu
            -5                  1               5

Gly Pro Gln Asp Arg Ser Ser Gln Gln Lys Gly Arg Leu Ser Leu Gln
        10                  15                  20

Asn Thr Ala Glu Ile Gln His Cys Leu Val Asn Ala Gly Asp Val Gly
    25                  30                  35                  40

Cys Gly Val Phe Glu Cys Phe Glu Asn Asn Ser Cys Glu Ile Gln Gly
                45                  50                  55

Leu His Gly Ile Cys Met Thr Phe Leu His Asn Ala Gly Lys Phe Asp
            60                  65                  70

Ala Gln Gly Lys Ser Phe Ile Lys Asp Ala Leu Arg Cys Lys Ala His
        75                  80                  85

Ala Leu Arg His Lys Phe Gly Cys Ile Ser Arg Lys Cys Pro Ala Ile
    90                  95                  100

Arg Glu Met Val Phe Gln Leu Gln Arg Glu Cys Tyr Leu Lys His Asp
105                 110                 115                 120

Leu Cys Ser Ala Ala Gln Glu Asn Val Gly Val Ile Val Glu Met Ile
            125                 130                 135

His Phe Lys Asp Leu Leu His Glu Pro Tyr Val Asp Leu Val Asn
        140                 145                 150

Leu Leu Leu Thr Cys Gly Glu Asp Val Lys Glu Ala Val Thr Arg Ser
    155                 160                 165

Val Gln Ala Gln Cys Glu Gln Ser Trp Gly Gly Leu Cys Ser Ile Leu
170                 175                 180

Ser Phe Cys Thr Ser Asn Ile Gln Arg Pro Pro Thr Ala Ala Pro Glu
185                 190                 195                 200

His Gln Pro Leu Ala Asp Arg Ala Gln Leu Ser Arg Pro His His Arg
            205                 210                 215

Asp Thr Asp His His Leu Thr Ala Asn Arg Gly Ala Lys Gly Glu Arg
        220                 225                 230

Gly Ser Lys Ser His Pro Asn Ala His Ala Arg Gly Arg Thr Gly Gly
        235                 240                 245

Gln Ser Ala Gln Gly Pro Ser Gly Ser Ser Glu Trp Glu Asp Glu Gln
    250                 255                 260
```

```
Ser Glu Tyr Ser Asp Ile Arg Arg
265                 270
```

(2) INFORMATION FOR SEQ ID NO:15:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (vii) IMMEDIATE SOURCE:
        (B) CLONE: ZC6172

(xi) SEQUENCE DESCRIPTION: SEQ ID NO:15:

```
GTCGGTGCTC AGCATTCACT ACTCGAGGGT TTTTTTTTTT TTTTTTT                47
```

(2) INFORMATION FOR SEQ ID NO:16:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (vii) IMMEDIATE SOURCE:
        (B) CLONE: ZC12453

(xi) SEQUENCE DESCRIPTION: SEQ ID NO:16:

```
CATCAGCCCC TGGCAGACAG GGCTCAGCTC TCCAGGCCTC                        40
```

(2) INFORMATION FOR SEQ ID NO:17:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (vii) IMMEDIATE SOURCE:
        (B) CLONE: ZC982

(xi) SEQUENCE DESCRIPTION: SEQ ID NO:17:

```
AATTCCCCTC CCGCGAAGGC GTCGGCGCGG GGCTGGCGTA GGGCCTGCGT CAGCTGCAGC    60

CCGCCGGAGC T                                                       71
```

(2) INFORMATION FOR SEQ ID NO:18:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (vii) IMMEDIATE SOURCE:
        (B) CLONE: ZC983

(xi) SEQUENCE DESCRIPTION: SEQ ID NO:18:

```
CCGGCGGGCT GCAGCTGACG CAGGCCCTAC GCCAGCCCCG CGCCGACGCC TTCGCGGGAG    60

GGG                                                                63
```

(2) INFORMATION FOR SEQ ID NO:19:

(i) SEQUENCE CHARACTERISTICS:
        (A) LENGTH: 38 base pairs
        (B) TYPE: nucleic acid
        (C) STRANDEDNESS: single
        (D) TOPOLOGY: linear -continued (vii) IMMEDIATE SOURCE:
(B) CLONE: ZC3509

(xi) SEQUENCE DESCRIPTION: SEQ ID NO:19:

CAAATTGACG TCATGGTAAA AATTGACGTC ATGGTAAG                38

(2) INFORMATION FOR SEQ ID NO:20:

(i) SEQUENCE CHARACTERISTICS:
(A) LENGTH: 46 base pairs
(B) TYPE: nucleic acid
(C) STRANDEDNESS: single
(D) TOPOLOGY: linear (vii) IMMEDIATE SOURCE:
(B) CLONE: ZC3510

(xi) SEQUENCE DESCRIPTION: SEQ ID NO:20:

AATTCTTACC ATGACGTCAA TTTTTACCAT GACGTCAATT TGAGCT       46

(2) INFORMATION FOR SEQ ID NO:21:

(i) SEQUENCE CHARACTERISTICS:
(A) LENGTH: 39 base pairs
(B) TYPE: nucleic acid
(C) STRANDEDNESS: single
(D) TOPOLOGY: linear (vii) IMMEDIATE SOURCE:
(B) CLONE: ZC12303

(xi) SEQUENCE DESCRIPTION: SEQ ID NO:21:

CCGGGTACCA TGTGTGCCGA GCGGCTGGGC CAGTTCATG               39

(2) INFORMATION FOR SEQ ID NO:22:

(i) SEQUENCE CHARACTERISTICS:
(A) LENGTH: 20 base pairs
(B) TYPE: nucleic acid
(C) STRANDEDNESS: single
(D) TOPOLOGY: linear (vii) IMMEDIATE SOURCE:
(B) CLONE: ZC12773

(xi) SEQUENCE DESCRIPTION: SEQ ID NO:22:

CCCCAAGAGA CACAGGAAGG                                    20

STANNIOCALCIN-2

CROSS REFERENCE TO RELATED APPLICATIONS

This application is related to Provisional Applications Ser. No. 60/015,137, filed on Apr. 2, 1996; Ser. No. 60/017,838, filed on Jun. 4, 1996; and Ser. No. 60/034,752, filed on Jan. 10, 1997. Under 35 U.S.C. § 119(e)(1), this Application claims benefit of said Provisional Applications.

BACKGROUND OF THE INVENTION

Maintaining electrolyte homeostasis is critical for preserving a cell's ability to interact with other cells and transduce signals that are mediated by changes in the environment. The levels of $Ca^{++}$ and $P_i$ in extracellular fluid is tightly regulated, and excitability of nerve and muscle are dependent upon ion concentration. In vertebrates parathyroid hormone (PTH), active metabolites of vitamin D and calcitonin have been identified as regulators of plasma levels of $Ca^{++}$ and $P_i$. PTH stimulates the mobilization of $Ca^{++}$ and $P_i$ from bone into plasma. In the kidneys, PTH decreases the urinary excretion of $Ca^{++}$ and stimulates excretion of $P_i$. $P_i$ reabsorption is reduced by decreasing the $Na^+$-dependent $P_i$ transport into the renal proximal tubule. Calcitonin is a hormone released by the thyroid that lowers $Ca^{++}$ and $P_i$ levels in the blood to maintain the equilibrium when serum levels are elevated. Calcitonin is believed to counteract hypercalcemia by inhibiting osteoclast-mediated bone resorption. However, the role of calcitonin as regulator of transient influcuations in serum calcium levels or promotion of bone mineralization has not been demonstrated. In addition, there are no known regulators of transient changes $P_i$ levels in mammals, other than PTH, which only promotes $P_i$ excretion, thereby suggesting that our understanding and identification of factors involved in the calcium and phosphate homeostasis is incomplete.

In fish, the environment can be either hypertonic (seawater) or hypotonic (fresh water) and is the primary source for $Ca^{++}$ and $P_i$, unlike terrestrial vertebrates whose uptake of $Ca^{++}$ and $P_i$ are diet dependent. Some fish migrate to and from seawater and fresh water and have had to develop mechanisms to adapt to these radical changes in electrolyte concentrations. Stanniocalcin (also known as Stc, CS protein, teleocalcin or hypocalcin) is a homodimeric glycoprotein hormone secreted by endocrine glands found on the kidneys of bony fish called the corpuscles of Stannius (Stannius, H. Arch. Anat. Physiol. 6:97–101, 1839 and Wagner, G., in *Biochemistry and Molecular Biolocy of Fishes*, eds. Hochachka and Mommsen, Elsevier Science, Amersterdam, Vol 2, Chap. 21, pp. 419–434, 1993). The secretion of stanniocalcin in fishes is stimulated in response to rising plasma $Ca^{++}$ levels (Wagner et al., *Mol. Cell Endocrinol.* 79:129–138, 1991) whereupon it acts to reduce $Ca^{++}$ uptake by the gills (Wagner et al., *Gen. Comp. Endocrinol.* 63:481–491, 1986) and increase $P_i$ reabsorption by the kidneys (Lu et al., *Am. J. Physiol.* 36:R1356–R1362, 1994) with the net result being restoration of normal calcium levels.

Stanniocalcin has been identified and isolated from several species of fish, such as Australian eel (*Auguilla australis*; Butkus et al., *Mol. Cell. Endocrinol* 54:123–134, 1987), rainbow trout (*Oncorhynchus mykiss*; Lafeber et al., *Gen. Comp. Endocrinol.* 69:19–30, 1988), coho salmon (*Oncorhynchus kisutch*; Wagner et al., *Mol. Cell. Endocrinol.* 90:7–15, 1992), and sockeye salmon (*Oncorhychus nerka*; Wagner et al., *Gen. Comp. Endocrinol.* 72:237–246, 1988. Studies using both in vivo and in vitro systems, show that in response to increased excellular $Ca^{++}$ levels, Stc is released. Stc reduces plasma $Ca^{++}$ concentration by inhibiting $Ca^{++}$ absorption across the intestine (Sundell et al., *J. Compl Physiol. B, Biochem Sys. Environ. Physiol.* 162:489–495, 1992) and $Ca^{++}$ transport across the gills (Wagner et al., ibid., 1988). In vivo, the rapid equilibration that occurs even when presented with massive increases in $Ca^{++}$ suggests that there may be additional pathways involved that have not yet been elucidated.

Human stanniocalcin has recently been discovered (Chang et al., *Mol. Cell. Endocrinol.* 112:241–247, 1995 and Olsen et al. WO 95/24411). The human protein is 247 amino acids, of which 214 amino acids constitute the mature polypeptide. It is believed that the first 33 amino acids represent a prepro region, consistent with Stc from fish, where the polypeptide is synthesized as a larger molecule and processed during secretion from the Corpuscles of Stannius. The human stanniocalcin discovered had a high degree of homology to the Australian eel; 119 identical amino acids in a 195 amino acid overlap (61% identity) and to coho salmon, 118 amino acids in a 204 amino acid overlap resulted in 57% identity. Eel and coho salmon Stc contain 15 and 12 cysteines respectively, while the human Stc has 11 cysteines. The spacing of the cysteines is highly conserved between all three proteins.

Human stanniocalcin mRNA was found to be most abundant in ovary, prostate and thyroid as a 4 kb transcript (Chang et al., *Mol. Cell. Endocrinol.* 112:241–247, 1995). The 4 kb band was also seen in kidney, bone marrow, thymic stromal cells (Olsen et al., *Proc. Natl. Acad. Sci. USA* 93:1792–1796, 1996) and many other tissues, but no signal was found in brain, liver, spleen, peripheral blood leukocytes and adrenal medulla. In addition, a 2 kb transcript was identified with a probe designed to a 1 kb N-terminal portion of the molecule but was not seen with a probe containing C-terminal sequence (Chang et al., ibid., 1995). Isolation of human stanniocalcin has been reported from an early stage lung cDNA library (Olsen et al., WO 95/24441). Sera from normal humans was immunoreactive with salmon Stc antibodies. Analyses by immunocytochemistry suggested that cells in the human kidney tubules contained Stc-like proteins (Wagner et al., *Proc. Natl. Acad. Sci. USA* 92:1871–1875, 1995).

Human stanniocalcin mRNA levels have been shown to increase in the presence of increasing amounts of excellular $Ca^{++}$ in an immortalized liver fibroblast cell line SUSM-1, T98G human glioblastoma cell line and normal human foreskin fibroblasts (Chang et al., ibid., 1995).

Because of the anti-hypercalcemic activity of stanniocalcin, members of the family, particularly human polypeptides will be very valuable in the understanding and treatment of diseases caused by electrolyte disorders. The present invention provides such polypeptides for these and other uses that should be apparent to those skilled in the art from the teachings herein.

SUMMARY OF THE INVENTION

Within one aspect, the present invention provides an isolated polynucleotide molecule encoding a stanniocalcin-2 (Stc2) polypeptide selected from the group consisting of (a) polynucleotide molecules comprising a nucleotide sequence as shown in SEQ ID NO: 1 from nucleotide 73 to nucleotide 906 or as shown in SEQ ID NO: 13 from nucleotide 73 to nucleotide 888; (b) allelic variants of (a); (c) polynucleotide molecules that encode a polypeptide that is at least 60% identical to the amino acid sequence of SEQ ID NO: 2 from amino acid residue 15 (Ser) to amino acid residue 184 (Leu); and degenerate nucleotide sequences of (a), (b), or (c).

Within a second aspect of the invention there is provided an expression vector comprising the following operably linked elements: a transcription promoter; a DNA segment selected from the group consisting of (a) polynucleotide molecules comprising a nucleotide sequence as shown in SEQ ID NO: 1 from nucleotide 73 to nucleotide 906 or as shown in SEQ ID NO: 13 from nucleotide 73 to nucleotide 888; (b) allelic variants of (a); (c) polynucleotide molecules that encode a polypeptide that is at least 600 identical to the amino acid sequence of SEQ ID NO: 2 from amino acid residue 15 (Ser) to amino acid residue 184 (Leu); and degenerate nucleotide sequences of (a), (b), or (c); and a transcription terminator.

Within a third aspect of the present invention there is provided a cultured cell into which has been introduced the expression vector described above, wherein said cell expresses the polypeptide encoded by the DNA segment.

A fourth aspect of the present invention provides an isolated and purified stanniocalcin-2 polypeptide. Within one embodiment, the isolated polypeptide is selected from the group consisting of (a) polypeptide molecules comprising an amino acid sequence as shown in SEQ ID NO: 2 from amino acid residue 1 to amino acid residue 278 or SEQ ID NO: 14 from amino acid residue 1 to amino acid residue 272; (b) allelic variants of (a); and polypeptides that are at least 60% identical to the amino acids of SEQ ID NO: 2 from amino acid residue 15 (Ser) to amino acid residue 184 (Leu).

Within another aspect of the present invention there is provided a pharmaceutical composition comprising purified stanniocalcin-2 in combination with a pharmaceutically acceptable vehicle.

Within another aspect of the present invention there is provided methods for producing stanniocalcin-2 comprising culturing a cell into which has been introduced the expression vector described previously, whereby said cell expresses a stanniocalcin-2 polypeptide encoded by the DNA segment and recovering the stanniocalcin-2 polypeptide.

BRIEF DESCRIPTION OF THE DRAWINGS

FIG. 1 illustrates a multiple alignment of salmon Stc (oncki); eel Stc (angau); human-1 Stc (stc1); human Stc2 (Zstc2); a partial sequence for hamster Stc2 and mouse Stc2. Within the FIGURE, certain amino acids in the hamster sequence were not determined but known to have a residue at that position. These undetermined amino acids are designated "X".

DETAILED DESCRIPTION OF THE INVENTION

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "expression vector" is used to denote a DNA molecule, linear or circular, that comprises a segment encoding a polypeptide of interest operably linked to additional segments that provide for its transcription. such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems.

"Operably linked", when referring to DNA segments, indicates that the segments are arranged so that they function in concert for their intended purposes, e.g. transcription initiates in the promoter and proceeds through the coding segment to the terminator The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

The present invention is based in part upon the discovery of a novel DNA sequence that encodes a polypeptide having homology to hypocalcemic proteins of the stanniocalcin family. Analysis of the tissue distribution of the mRNA corresponding to this novel DNA showed that expression was highest in pancreas, followed by apparent but decreased expression levels in heart, placenta, skeletal muscle, thyroid and spleen. The polypeptide has been designated Stanniocalcin-2 (Stc2).

The novel stanniocalcin-2 polypeptides of the present invention were initially identified by querying an EST database for homologous sequences to stanniocalcin. A single EST sequence was discovered and hypothesized to be related to the stanniocalcin family. The novel polypeptide encoded by the cDNA contained a cysteine motif of the formula:

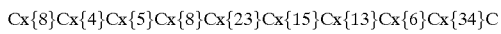

Cx{8}Cx{4}Cx{5}Cx{8}Cx{23}Cx{15}Cx{13}Cx{6}Cx{34}C wherein x{ } is the number of amino acid residues between cysteines (C). This cysteine motif occurs in all known members of the stanniocalcin family (for example, human, eel and salmon) and is unique to these proteins.

Figure 1:
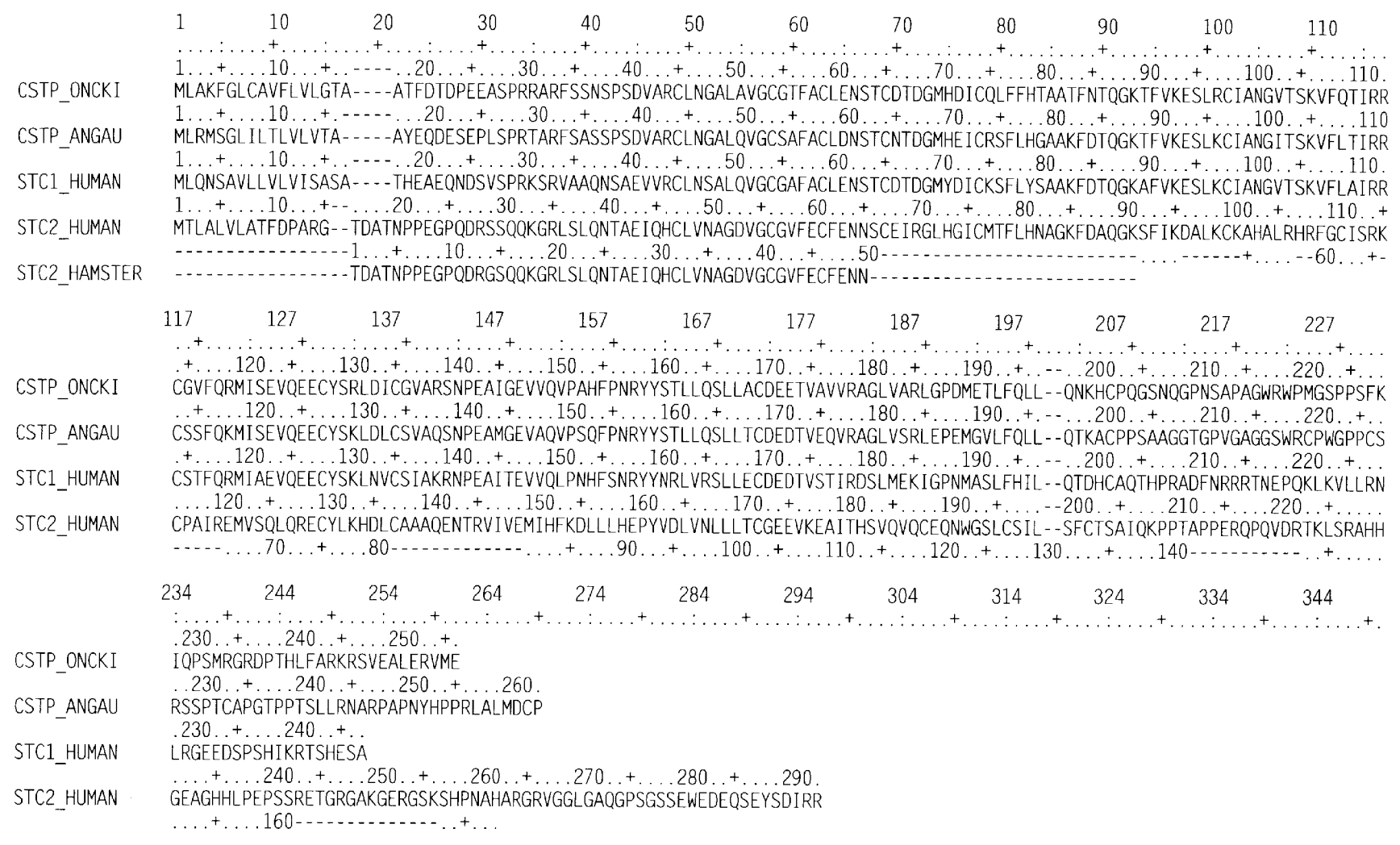

Analysis of the DNA encoding a stanniocalcin-2 polypeptide (SEQ ID NO: 1) revealed an open reading frame encoding 302 amino acids (SEQ ID NO: 2) comprising a signal peptide of 24 amino acid residues (residue −24 to residue −1 of SEQ ID NO: 2) and a mature polypeptide of 278 amino acids (residue 1 to residue 278 of SEQ ID NO: 2). A potential N-linked glycosylation site is present at amino acid residue 49 of SEQ ID NO: 2 of the mature polypeptide. Multiple alignment of stanniocalcin-2 with other known stanniocalcins revealed a block of high percent identity corresponding to amino acid residue 15 to amino acid residue 184 of SEQ ID NO: 2 and as is shown in FIG. 1. A multiple alignment also revealed a greater degree of divergence at the C-terminus of stanniocalcin than seen at the N-terminus. The divergent region in human Stc2 corresponds to amino acid residues 184 to amino acid residue 278 of SEQ ID NO: 2 and is shown in FIG. 1.

The mouse stanniocalcin-2 sequence was also identified from a mouse cDNA library generated from murine osteoblastic type cells. Analysis of the DNA encoding the mouse stanniocalcin-2 protein revealed an open reading from encoding 296 amino acids (SEQ ID NO: 14) comprising a signal peptide of 24 amino acids (amino acid residue −24 to residue −1 of SEQ ID NO: 14), and a mature polypeptide of 272 amino acids, residue 1 to residue 272 of SEQ ID NO: 14).

Within the N-terminal block of high identity, the following percent identity figures are observed between members of the stanniocalcin family:

|  | oncki | angau | human | STC2 |
|---|---|---|---|---|
| oncki Stc | 100 | 77.6 | 64.7 | 31.8 |
| angau Stc | 77.6 | 100 | 66.5 | 35.9 |
| human Stc | 64.7 | 66.5 | 100 | 37.6 |
| human Stc2 | 31.8 | 35.9 | 37.6 | 100 |

Those skilled in the art will recognize that the sequences disclosed in SEQ ID NOS: 1 and 13 represent a single allele of the human and mouse Stc2 polypeptide, respectively. Allelic variants of these sequences can be cloned by probing cDNA or genomic libraries from different individuals according to standard procedures.

The present invention further provides counterpart polypeptides and polynucleotides from other species ("species homologs"). of particular interest are Stc2 polypeptides from other mammalian species, including porcine, ovine, bovine, canine, feline, equine and other primate proteins. Species homologs of the human proteins can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue of cell line. A Stc2-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to the Stc2. Similar techniques can also be applied to the isolation of genomic clones.

The present invention also provides isolated Stc2 polypeptides that are substantially homologous to the polypeptides of SEQ ID NOS: 2 and 14 and their species homologs. By "isolated" is meant a protein or polypeptide which is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. The term "substantially homologous" is used herein to denote polypeptides having 50%, preferably 60%, more preferably at least 80%, sequence identity to the sequences shown in SEQ ID NOS: 2, 14 or their species homologs. Such polypeptides will more preferably be at least 90% identical, and most preferably 95% or more identical to SEQ ID NOS: 2, 14 or their species homologs. Percent sequence identity is determined by conventional methods. See, for example, Altschul et al., Bull. Math. Bio. 48: 603–616, 1986 and Henikoff and Henikoff, Proc. Natl. Acad. Sci. USA 89:10915–10919, 1992, both incorporated herein by reference. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 1 (amino acids are indicated by the standard one-letter codes).

TABLE 1

|  | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

The percent identity is then calculated as:

$$\frac{\text{Total number of identical matches}}{[\text{length of the longer sequence plus the number of gaps introduced into the longer sequence in order to align the two sequences}]} \times 100$$

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is soconservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See, in general Ford et al., *Protein Expression and Purification* 2: 95–107, 1991, which is incorporated herein by reference.

TABLE 2

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Essential amino acids in the polypeptides of the present invention can be identified according to procedures known in the art, such as site-directed mutagenesis or alanine-scanning mutagenesis (Cunningham and Wells, *Science* 244, 1081–1085, 1989). In the latter technique, single alanine mutations are introduced at every residue in the molecule, and the resultant mutant molecules are tested for biological activity (e.g. calcium modulation) to identify amino acid residues that are critical to the activity of the molecule.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis methods as disclosed above can be combined with high-throughput, automated screening methods to detect activity of cloned, mutagenized polypeptides in host cells. Mutagenized DNA molecules that encode active polypeptides (e.g., modulate calcium and phosphate levels) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that are substantially homologous to residues 1 to 278 of SEQ ID NO: 2, residues 1 to 272 of SEQ ID NO: 14 or allelic variants thereof and retain the electrolyte-modulating properties of the wild-type protein.

The polypeptides of the present invention can be isolated by exploitation of their interaction with divalent ions. The polypeptides contain a histidine-rich region in the C-terminus of the molecule that confers an affinity for chelated metal ions. For example, immobilized metal ion adsorption (IMAC) chromatography can be used where a gel is first charged divalent metal ions to form a chelate (Sulkowski E., *Trends in Biochem.* 3:1–7, 1985). Histidine-rich proteins will be adsorbed to the matrix with differing affinities, dependent upon the metal ion used, and eluted by competitive elution, lowering the pH, or use of strong chelating agents. Other methods of purification include, purification of glycosylated proteins by lectin affinity chromatography and ion exchange chromatography (*Methods in Enzymol.*, vol. 182, "Guide to Protein Purification", M. Deutscher, ed., Acad. Press, San Diego, 1990, pp.529–539, incorporated herein by reference).

The polypeptides of the present invention, including full-length proteins and fragments thereof, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly culture cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., ibid., which are incorporated herein by reference.

In general, a DNA sequence encoding a Stc2 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a Stc2 polypeptide into the secretory pathway of a host cell, a secretory signal sequence (also known as a leader sequence, prepro sequence or pre sequence) is provided in the expression vector. The secretory signal sequence may be that of the Stc2 polypeptide, or may be derived from another secreted protein (e.g., t-PA) or synthesized de novo. The secretory signal sequence is joined to the Stc2 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are also preferred hosts within the present invention. Methods for introducing exogenous DNA into mammalian host cells include calcium phosphate-mediated transfection (Wigler et al., *Cell* 14:725, 1978;

Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology*, John Wiley and Sons, Inc., NY, 1987), and liposome-mediated transfection (Hawley-Nelson et al., *Focus* 15:73, 1993; Ciccarone et al., *Focus* 15:80, 1993), which are incorporated herein by reference. The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463, which are incorporated herein by reference. The use of *Agrobacterium rhizogenes* as a vector for expressing genes in plant cells has been reviewed by Sinkar et al., *J. Biosci.* (Bangalore) 11:47–58, 1987.

Fungal cells, including yeast cells, and particularly cells of the genus Saccharomyces, can also be used within the present invention, such as for producing Stc2 fragments or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by the selectable marker, commonly drug resistance or the ability to grow in the absence of a particular nutrient (e.g. leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia guillermondii* and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

The activity of molecules of the present invention can be measured using a variety of assays that measure changes in electrolyte concentrations. Of particular interest are changes in calcium and phosphorus levels. Such assays are well known in the art. For a general reference, see *Cellular Calcium: A Practical Approach*, McCormack and Cobbold, eds., Oxford University Press, NY, 1991, which is incorporated herein by reference. Specific assays include, but are not limited to bioassays measuring calcium and phosphorus levels in urine and plasma of cannulated mice (Olsen et al., *Proc. Natl. Acad. Sci. USA* 93:1792–1796, 1996); $P_i$ resorption by kidney cells (Lu et al., 1994, ibid.); $Ca^{++}$ uptake by osteoblasts (Whitson et al., *J. Bone Miner. Res.* 7:727–741, 1992), and $Ca^{++}$ uptake by fish gills (Wagner et al., *Proc. Natl. Acad. Sci. USA* 92:1871–1875, 1995) and calvarial assays that measure bone resorption and increases in free $Ca^{++}$ (Linkhart et al., *Endocrinol.* 125:1484–1491, 1989).

Proteins of the present invention are useful for modulating calcium serum levels. Changes in calcium flux levels can be measured in vitro using cultured cells for in vivo by administering molecules of the claimed invention to the appropriate animal model. For instance, Stc2 transfected (or co-transfected) expression host cells may be embedded in an alginate environment and injected (implanted) into recipient animals. Alginate-poly-L-lysine microencapsulation, permselective membrane encapsulation and diffusion chambers have been described as a means to entrap transfected mammalian cells or primary mammalian cells. These types of non-immunogenic "encapsulations" or microenvironments permit the transfer of nutrients into the microenvironment, and also permit the diffusion of proteins and other macromolecules secreted or released by the captured cells across the environmental barrier to the recipient animal. Most importantly, the capsules or microenvironments mask and shield the foreign, embedded cells from the recipient animal's immune response. Such microenvironments can extend the life of the injected cells from a few hours or days (naked cells) to several weeks (embedded cells).

Alginate threads provide a simple and quick means for generating embedded cells. The materials needed to generate the alginate threads are readily available and relatively inexpensive. Once made, the alginate threads are relatively strong and durable, both in vitro and, based on data obtained using the threads, in vivo. The alginate threads are easily manipulable and the methodology is scalable for preparation of numerous threads. In an exemplary procedure, 3% alginate is prepared in sterile $H_2O$, and sterile filtered. Just prior to preparation of alginate threads, the alginate solution is again filtered. An approximately 50% cell suspension (containing about 5×105 to about 5×107 cells/ml) is mixed with the 3% alginate solution.

One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle attached). A large bore needle is then attached to the syringe, and the thread is intraperitoneally injected into a recipient in a minimal volume of the Lactated Ringer's Solution.

Stc2 polypeptides can also be used to prepare antibodies that specifically bind to Stc2 proteins or polypeptides. Immunogens may be full-length or portions of molecules may be combined with a carrier, if "hapten-like". As used herein, the term "antibodies" includes polyclonal antibodies, monoclonal antibodies, antigen-binding fragments thereof such as F(ab')$_2$ and Fab fragments, and the like, including genetically engineered antibodies. Antibodies are defined to be specifically binding if they bind to a Stc2 polypeptide with a $K_a$ of greater than or equal to $10^7$/M. The affinity of an antibody can be readily determined by one of ordinary skill in the art (see, for example, Scatchard, ibid.).

Methods for preparing polyclonal and monoclonal ntibodies are well known in the art (see for example, ambrook et al., i Molecular Cloning: A Laboratory Manual, Second Edition, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982, which are incorporated herein by reference). As would be evident to one of ordinary skill in the art, polyclonal antibodies can be generated from a variety of warm-blooded animals such as horses, cows, goats, sheep, dogs, chickens, rabbits, mice, and rats. The immunogenicity of a Stc2 polypeptide may be increased through the use of an adjuvant such as Freund's complete or incomplete adjuvant. A variety of assays known to those skilled in the art can be utilized to detect antibodies which specifically bind to Stc2 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immunosorbent assays (ELISA), dot blot or Western blot assays, inhibition or competition assays, and sandwich assays. A preferred assay system employing a ligand-binding receptor fragment uses a commercially available biosensor instrument (BIAcore™, Pharmacia Biosensor, Piscataway, N.J.), wherein the receptor fragment is immobilized onto the surface of a receptor chip. Use of this instrument is disclosed by Karlsson, *J. Immunol. Methods* 145:229–240, 1991 and Cunningham and Wells, *J. Mol. Biol.* 234:554–563, 1993. A receptor fragment is covalently attached, using amine or sulfhydryl chemistry, to dextran fibers that are attached to gold film within the flow cell. A test sample is passed through the cell. If ligand is present in the sample, it will bind to the immobilized receptor polypeptide, causing a change in the refractive index of the medium, which is detected as a change in surface plasmon resonance of the gold film. This system allows the determination of on- and off-rates, from which binding affinity can be calculated, and assessment of stoichiometry of binding.

Antibodies to Stc2 may be used for isolating for affinity purification, for diagnostic assays for determining circulating levels of Stc2 polypeptides, and as antagonists to block Stc2 binding and signal transduction in vitro and in vivo.

Molecules of the present invention can be used to identify and isolate receptors involved in electrolyte homeostasis. For example, proteins and peptides of the present invention can be immobilized on a column and membrane preparations run over the column (*Immobilized Affinity Ligand Techniques*, Hermanson et al., eds., Academic Press, San Diego, Calif., 1992, pp.195–202). Proteins and peptides can also be radiolabeled (*Methods in Enzymol.*, vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

The molecules of the present invention will be useful for removing $Ni^{++}$, $Ca^{++}$ and other divalent ions from solutions where the presence of such ions are a toxic contaminant.

The polypeptides, nucleic acid and/or antibodies of the present invention may be used in treatment of disorders associated with changes in electrolyte homeostasis, particularly disorders caused by, or resulting in, changes in calcium, phosphate, magnesium, zinc and copper levels. The molecules of the present invention may used to modulate electrolyte imbalances or to treat or prevent development of pathological conditions in such diverse tissue as bone, heart, kidney, pancreas and the vascular system. In particular, certain bone diseases, hypertension, renal failure, hyperthyroidism, hyperparathyroidism, certain carcinomas, sarcoidosis, pancreatitis and drug-induced disorders that result in elevated levels of serum calcium, known as hypercalcemia, may be amenable to such diagnosis, treatment or prevention.

Parathyroid hormone (PTH) and parathyroid hormone-related protein (PTHRP) stimulate osteoclasts to resorb bone and are believed to provide the primary pathogenic mechanism for hypercalcemia. Certain cytokines have been shown to stimulate osteoclasts (including interleukin 1α, interleukin 1β, tumor necrosis factor-α, lymphotoxin, and transforming growth factor-α) and may play a role in hypercalcemia. Also, excessive a gastrointestinal absorption of calcium can lead to hypercalcemia and has been correlated with pancreatitis.

Increased serum phosphorus is also associated with hypercalcemia. Molecules of the present invention can be used to treat calcium-phosphorus imbalance. Elevated levels of serum calcium and phosphorus can result in bone and muscle pain, and molecules of the present invention would play a role in treating these disorders by modulating the serum calcium levels. In addition, calcium-phosphorus imbalances can lead to deposition of calcium in organs such as brain, eyes, myocardium and blood vessels.

Depressed levels of serum calcium, or hypocalcemia, can lead to increased resorption of calcium from bone. Increased bone resorption can result in osteoporosis and Paget's disease. Molecules of the present invention can be used to identify and, in some cases treat, diseases where calcium regulation is abnormal.

Hypomagnesium can occur because of reduced magnesium intake, reduced resorption and/or increased excretion. These conditions result from various disease states, that include hypercalcemia, hyperthyroidism, primary hyperparathyroidism, hungry bone syndrome, Bartter's syndrome, Gitelaman's syndrome, necrotizing enterocolitis and diabetes. Hypomagnesium (and the associated pertebation of mineral homeostasis that is caused by the imbalance) can contribute to the development of atherosclerosis, myocarial infarction, hypertension, cancer, renal stones, PMS, and has been correlated to insulin resistance. Hypomagnesium is often associated with renal failure.

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a Stc2 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses will generally be in the range of 0.1 to 100 µg/kg of patient weight per day, preferably 0.5–20 µg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of Stc2 is an amount sufficient to produce a clinically significant change in serum electrolyte levels. For example, normal ranges for serum calcium levels are in the range of 8.5–10.5 mg/dl or 2.1–2.5 mM. Treatment would generally begin when serum calcium levels drop below 7.5 mg/dL (1.9 mM) or above 12 mg/dL. Generally, inorganic phosphate serum levels below 1.0–2.0 mg/dl require treatment.

EXAMPLES

Example 1

Scanning of a translated DNA database using a salmon stanniocalcin as a query resulted in identification of an expressed sequence tag (EST) sequence found to be homologous to positions 19–127 of the eel stanniocalcin sequence (shown in FIG. 1) and designated Zstc2.

Oligonucleotides primers ZC10189 (SEQ ID NO: 4) and ZC10191 (SEQ ID NO: 5) were designed to begin priming internally within the EST, and were used to recreate 208 of the 333 bp of the EST sequence. Poly $A^+$ RNA was isolated from a panel of sources (see Table 3) and was used to prepare a cDNA library with a Marathon™ cDNA Amplification Kit (Clontech, Palo Alto, Calif.) using the protocol provided by the manufacturer.

TABLE 3

| |
|---|
| human spleen |
| human umbilical vein endothelial cells |
| T47D human mammary carcinoma line |
| human placenta |
| human pancreas |
| human skeletal muscle |
| human fetal lung |
| K562, human chronic myelogenous cell line |
| human liver |
| HuH7, human liver cell line |

The conditions used for the PCR reaction were 1 cycle at 94° C. for 30 seconds, 35 cycles at 94° C. for 1 minute; 68° C. for 1 minute; 72° C. for 3 minutes, followed by 1 cycle for 10 minutes at 72° C. and 4° C. incubation period. The PCR reaction confirmed that EST sequence was correct, and identified K562 and T47D libraries as having a high probability of containing a cDNA for the EST sequence. Other libraries that could be amplified with the oligonucleotide primers included liver, spleen, and placenta.

T47D, K562, placenta, and liver "marathon ready" cDNA libraries were amplified by PCR with oligonucleotide primers ZC10189 (SEQ ID NO: 4) and ZC10191 (SEQ ID NO: 5), using slightly modified conditions: 94° C. for 1.5 minutes, 35 cycles of 94° C. for 30 seconds and 70° C. for 1 minute, followed by 1 cycle at 72° C. for 10 minutes and 4° C. incubation period.

The amplified DNA was electrophoresed on a 1.2% low melting agarose gel and gel purified. The resulting T47D- and K562-generated DNA fragments were 208 bp in length. The DNA fragments were purified on WIZARD DNA extraction columns (Promega, Madison, Wis.). Purified DNA was used in a ligation reaction using the pGEM-T (Promega) vector system, according to the manufacturer's specification. The plasmid DNA was used to transform electro-competent DH10b *E. coli* cells by electroporation.

Colonies were screened by PCR using EST-specific primers. Individual white colonies representing recombinants were picked and added to microcentrifuge tubes by swirling the toothpick with the colony on it in a tube containing 11.0 µl $H_2O$, 2.0 µl 10× Taq polymerase buffer (Boehringer Mannheim, Indianapolis, Ind.), 2.0 µl 2 mM dNTPs, 1.0 µl ZC694 (SEQ ID NO: 6) (20 pmol/µl), 10 µl ZC695 (SEQ ID NO: 7) (20 pmol/µl), and 1.0 µl Taq polymerase. Cells were streaked out on a master plate to use for starting cultures. Amplification reactions were incubated at 95° C. for 1 minute 20 seconds to lyse the bacteria and expose the plasmid DNA, then run for 25 cycles of 94° C., 20 seconds; 30° C. for 45 seconds; 72° C. for 1 minute to amplify cloned inserts. Products were analyzed by electrophoresis on a 1% agarose gel. Twelve clones were identified as positive, and plasmid templates were prepared for sequencing of 2 clones, one from T47D cDNA and the other from k562 cDNA, using a QIAwell™ 8 Plasmid Kit (Qiagen Inc., Chatsworth, Calif.). Identical sequence was seen using both cell types confirming the 208 bp of the EST sequence and identifying a previously unidentified nucleotide (N) in the EST at position 201 as a Cytosine (C).

A 5' RACE (rapid amplification of cDNA ends) reaction was used to generate additional cDNA sequence as follows: a K562 "marathon ready" cDNA library was used as template in a PCR reaction with oligonucleotide ZC10191 (SEQ ID NO: 5) and the marathon primer AP-2 (Clontech) for 35 cycles at 94° C. for 1.5 minutes; 94° C. for 30 seconds and 70° C. for 1 minute, followed by 1 cycle at 72° C. for 10 minutes and 4° C. incubation period. Several bands resulted and 3 different regions of the gel were isolated and purified using WIZARD columns (Promega). The DNA resulting from the various bands were used in a PCR reaction (as described above) and only one band, a DNA fragment slightly larger than the 310 bp marker, was amplified and was identified as the correct sequence by PCR reaction. The >310 bp fragment was gel purified using a WIZARD column (Promega), ligated into pGEM-T, transformed into DH10b cells, and white colonies were isolated and sequenced, as described above. Two differences between the EST sequence and our 5' RACE products were identified. First, position 31 where a C was present in the EST was not present in the 5' RACE product. Second, position 76's Guanidine (G) in the EST was not present in our 5' RACE product. This resulted in 2 frame shifts which, when aligned with the stanniocalcin family appeared to give a correct alignment because the cysteines were aligned with very few amino acid differences between Stc2 and other members of the stanniocalcin family. The Met start codon was in the expected location and a signal sequence and cleavage site were seen.

A 3' RACE product was generated using a "marathon ready" human kidney cDNA library as template and AP-1 (Clontech) and oligonucleotide ZC10130 (SEQ ID NO: 9) as primers. A PCR reaction was run as follows: 30 cycles at 98° C. for 20 seconds; 60° C. for 20 seconds; 68° C. for 2 minutes and 1 cycle at 68° C. for 5 minutes. An aliquot of DNA was removed and analyzed on a 1.5% agarose gel. Multiple bands were seen on the gel. The remaining DNA was purified on a CHROMASPIN 100® spin column (Clontech) to remove unincorporated nucleotides and primers. A second inner-nested PCR reaction was run to amplify template DNA sequence. The PCR reaction used AP-2 (Clontech) and oligonucleotide ZC10,139 (SEQ ID NO: 8), which was designed to hybridize to EST sequence internal of ZC10130 (SEQ ID NO: 9). The PCR reaction was run for 30 cycles at 98° C. for 20 minutes, 30 cycles at 60° C. for 20 minutes, 30 cycles at 68° C. for 2 minutes and 1 cycle at 68° C. for 5 minutes. The resulting DNA products were electrophoresed on a 1.5% agarose gel and bands at approximately 1.7 kb, 1.8 kb and 3.0 kb were seen. The DNA bands were gel purified and sequenced. Sequence analyses revealed that the DNA products included the EST DNA sequence.

Using sequence generated from both the 5' and 3' RACE products, oligonucleotides were designed to provide primers for sequencing the entire full-length cDNA. Oligonucleotide ZC10772 (SEQ ID NO: 10) was designed to hybridize 5' of the signal sequence to 11 base pairs into the signal sequence and generated a BamH I site at the 5' of PCR product. Oligonucleotide ZC10773 (SEQ ID NO: 11) was designed to hybridize 44 base pairs beyond the 3' end of the Zstc2 gene and generated an EcoR I site at the 3' of the PCR product. Marathon ready cDNA libraries from K562 and T57D cells (Clontech) were used as template in the PCR reaction. The PCR reaction was as followed: one cycle at 94° C. for 1 minute; 30 cycles at 94° C. for 30 seconds, 60° C. for 20 seconds, 72° C. for for 2 minutes; followed by 72° C. for 10 minutes and held at 4° C. The PCR products were run on 1% low melt agarose gels and 1 kb DNA fragments were isolated. The DNA fragments were confirmed to have the same sequence by direct sequence analysis.

The PCR reactions were repeated, as above, to generate more DNA, and phenol-chloroform extracted and ethanol precipitated. The resuspended DNA was digested with EcoR I and BamH I and ligated in a cloning vector pHZ-1. Plasmid pHZ-1 is an expression vector that may be used to express protein in mammalian cells or in a frog oocyte translation system from mRNAs that have been transcribed in vitro. The pHZ-1 expression unit comprises the mouse metallothionein-1 promoter, the bacteriophage T7 promoter flanked by multiple cloning banks containing unique restriction sites for insertion of coding sequences, the human growth hormone terminator and the bacteriophage T7 terminator. In addition, pHZ-1 contains an E. coli origin of replication; a bacterial beta lactamase gene; a mammalian selectable marker expression unit comprising the SV40 promoter and origin, a neomycin resistance gene and the SV40 transcription terminator. To facilate directional cloning into pHZ-1, a polymerase chain reaction employing appropriate primers was used to create an EcoR I site and a Xho I site upstream from the translation initation codon and downstream from the translation termination codon, respectively.

Several clones were sequenced and a consensus sequence was identified. A clone designated 16—16, generated from T47D cDNA was identified to contain the consensus sequence and used to transfection into mammalian cells.

A further analysis of the cDNA sequence revealed that the 16—16 clone was missing nucleotides 1 to 27 of SEQ ID NO: 1 at the 5' end of the polynucleotide sequence. The missing polynucleotide sequence was added by ligation of of a PCR fragment generated by oligonucleotides ZC12303 (SEQ ID NO: 21) that included a Kpn I cloning site, the stc2 Kozak sequence and the missing polynucleotide sequence at the 5' end and ZC12773 (SEQ ID NO: 22) at the 3' end.

Example 2

Northerns were performed using Human Multiple Tissue Blots from Clontech (Palo Alto, Calif.). The probe was designed from a 5' RACE product (see Example 1) which had been subcloned into PGEM-T and was designated 7–51. Using AP2 (Clontech) and oligonucleotide ZC10191 (SEQ ID NO: 5) as primers, the RACE insert was reamplified in a PCR reaction as follows: 94° C. for 1.5 minutes, 35 cycles of 94° C. for 30 seconds and 70° C. for 1 minute, followed by 1 cycle at 72° C. for 10 minutes and 4° C. incubation period. The resulting DNA fragment was electrophoresed on a 1% agarose gel, the fragment was electroeluted, and then radioactively labeled using a randon priming MEGAPRIME DNA labeling system (Amersham, Arlington Heights, Ill.) according to the manufacturer's specifications. The probe was purified using a NUC TRAP® push column (Stratagene, La Jolla, Calif.). EXPRESSHYB® (Clontech, Palo Alto, Calif.) solution was used for prehybridization and as a hydrizing solution for the Northern blots. Hybridization took place at 60° C. and the blots were washed in 2×SSC and 0.05% SDS at RT followed by a wash in 0.1×SSC and 0.1% SDS at 50° C. Two transcript sizes were observed, one at approximately 4.4 kb, one at 2 kb. Signal intensity was highest for pancreas, with relatively less intense signals in heart, placenta, skeletal muscle, spleen, prostate and uterus. Weaker signals were present in thyroid, spinal cord, trachea, and small intestine.

Example 3

A.

A protein found in baby hamster kidney cell conditioned medium (BHK 570 cells; ATCC Accession No. 10314) was purified and characterized and found to be highly homologous to Zstc2. The protein was isolated as retentate on a $Ni^{++}$ column, microsequenced and designated "Factor x".

Conditioned medium was collected from BHK cells grown in a cell factory (Nunc, Naperville, Ill.) in serum free medium (see Table 4) for 48 hours. The medium was filtered through a 0.45 μM VERSAFLOW® Capsule Filter (Gelman Sciences, Ann Arbor, Mich.).

TABLE 4

Serum-free Medium 500 ml Dulbecco's Modified Eagle's Medium (DMEM; Gibco BRL)
(1mM) sodium pyruvate (Irvine, Santa Ana, CA)
(.29 mg/ml) L-glutamine (Hazelton, Lenexa, KS)
(1 mg/ml) vitamin K (Merck, Whitehouse Station, NJ)
(10 mg/ml) transferrin (JRH, Lenexa, KS)
(5 mg/ml) fetuin (Aldrich, Milwaukee, WI)
(5 mg/ml) insulin (Gibco BRL)
(2 ug/ml) selenium (Aldrich, Milwaukee, WI)

After filtration, the filtrate was concentrated 30 to 100-fold on an Amicon DC 10L concentrator (Amicon, Beverly, Mass.) using a 10,000 molecular weight cutoff hollow fiber ultrafiltration membrane (AG Technology, Needham, Mass.). The concentrate was buffer exchanged on the same ultrafiltration column using a buffer containing 20 mM $NaPO_4$, 0.5 M NaCl, 10 mM imidazole at pH 7.4 (Buffer A).

The filtrate was loaded onto a NTA agarose $Ni^{++}$ resin (Qiagen Inc., Chatsworth, Calif.) and washed to baseline using Buffer A. The filtrate was washed again in a Buffer A that contained 20 mM imidazole. The column was eluted with Buffer A containing 0.5 M imidazole and aliquots from the fractions were assayed by SDS-PAGE and transferred to nitrocellulose for Western blot analyses.

Fractions enriched in "Factor x" were pooled and dialyzed against 20 mM Tris pH 8.0. The dialyzed solution was applied to a Source Q column (Pharmacia LKB Biotechnology, Piscataway, N.J.) and eluted in a 20 minute gradient from 0–0.5 M NaCl. Aliquots of the fractions were assayed by SDS-PAGE and analyzed by commassie blue staining. The analysis revealed several bands present at 50–65 kDa.

B.

Purified "factor x" was isolated by electrophoresis under reducing and non-reducing conditions on 4–20% Tris/Glycine SDS-PAGE gels (Novex, Encinitas, Calif.) and electroblotted onto a poly(vinylideme difluoride) (PVDF) membrane (Applied Biosystems, Inc., Foster City, Calif.). From the reduced sample two bands of approximately 30 and 33 kDa were excised, and from the non-reduced sample a heterogenous band of approximately 60 kDa was excised. The N-terminal amino acid sequence of these bands was determined with an Applied Biosystems Model 470A (Foster City, Calif.) sequencer using the manufacturer's programming and chemicals. All three sequence analyses resulted in a single 30-amino acid $NH_2$-terminal sequence (SEQ ID NO: 3) Internal fragments were generated by trypsin digestion of "factor x" on PVDF. Tryptic fragments were resolved by HPLC and sequenced.

MALDI time-of-flight mass spectra were determined for purified, unreduced "factor x" using a TofSpec SE mass spectrometer (Micromass Instruments, Beverly, Mass.) equipped with a UV laser at 337 nm. Full scale laser output was measured to be 180 μJ/shot with a 4 ns pulse width, and the laser was attenuated using the OPUS software system (Micromass Instruments). The laser course adjustment was set at 20% transmittance and the fine adjustment was varied between 70% and 100% transmittance. All spectra were measured in the linear TOF mode (1.5 m flight path). The target was held at 25 kV with an extraction voltage of 8.3 kV and a focus voltage of 23 kV; the detector was held at 3.8 kV.

The sample and internal control were prepared by pre-mixing 1 μl of 1 pmol human transferrin and 1 μl purified, unreduced "factor x" (~1 pmole) with 1.5 μl of sinapinic acid in 30% $CH_3CN$/706 $H_2O$/0.1% TFA. 2.5 μl were spotted on the target and allowed to air dry at room temperature. Mass spectra were generated from the average of 10 shots and the summation of 10 spectra, thus 100 shots total. An OPUS software-determined smoothing was applied, allowing a peak detection of the internal standards at 80% baseline with 0.2506 peak slope. Two species with mass of 61,871+/−600 amu and 64,121+/−600 amu were detected. A second MALDI using reduced, alkylated "factor x" was performed as above and gave two species of mass 29,928+/−250 amu and 32,592+/−250 amu. The differences in mass between the two species may be due to glycosylation or C-terminal differences.

C.

Polyclonal anti-peptide antibodies were prepared by immunizing male Sprague-Dawley rats and New Zealand White rabbits with a peptide corresponding to the 30 amino acid N-terminal segment from "factor x" (SEQ ID NO: 3), which was synthesized using an Applied Biosystems Model 431A peptide synthesizer (Applied Biosystems, Inc., Foster City, Calif.) according to manufacturer's instructions. The peptide was conjugated to the carrier protein keyhole limpet hemocyanin (KLH) with gluteraldehyde. The rats were each given an initial intraperitoneal (ip) injection of 300 μg of peptide in Complete Freund's Adjuvant followed by booster ip injections of 150 μg peptide in Incomplete Freund's Adjuvant every two weeks. Rabbits were each given an initial subcutaneous injection of 600 μg of peptide in Complete Freund's Adjuvant, followed by booster subcutaneous injections of 300 μg of peptide in Incomplete Freund's Adjuvant every three weeks. Five days after the administration of the third booster injection, the animals were bled and the serum was collected. The animals were then boosted and bled every two weeks.

"Factor x" peptide-specific antibodies were affinity purified from the serum using a CNBr-SEPHAROSE 4B-peptide column (Pharmacia LKB) that was prepared using 20 mg of the 30 amino acid $NH_2$-terminal peptide (SEQ ID NO: 3) per gram CNBr-Sepharose, followed by dialysis in PBS overnight. Both rat and rabbit "Factor x"-specific antibodies were characterized by a sandwich ELISA titer check using 5 μg/ml of the 30 amino acid $NH_2$-terminal peptide (SEQ ID NO: 3) used to make the antibodies. The lower limit of detection (LLD), the lowest dilution exhibiting an OD which is 3x over background, for both rat and rabbit antibodies was 1 ng/ml antibody when combined with 5 μg/ml peptide. Western blot analysis of the affinity purified "Factor x" antibodies showed that each antibody preparation specifically recognized the 30 and 33 kD bands under reducing conditions and a heterogenous region consisting of 3–4 bands around 60 kDa under non-reducing SDS-PAGE of "factor x".

Example 4

Calvaria, which included parietal bone with the sagital suture, were collected from 4-day old CD-1 mice (Charles River Laboratories, San Diego, Calif.). The bones were placed in 6 well petri dishes (American Science Products, McGraw Park, Ill.) with 1 ml of growth medium (DMEM, 0.29 mg/ml L-glutamine, 1 mM sodium pyruvate, and 15% heat inactivated horse serum (HIHS)) and incubated at 37° C. in 50% $CO_2$ shaking gently for 24 hours. After the incubation, the medium was removed from the wells and replaced with 1.5 ml growth medium containing Zs.

Zstc2 at 10 ng/ml, 100 ng/ml, 760 ng/ml or control without Zstc2. Five bones were in each sample group, and the groups were incubated rocking at 37° C., 5% $CO_2$ for 72 hours. After the incubation, the medium was removed from the wells and analyzed for $Ca^{++}$ levels using a NOVA-7 total calcium analyzer (Nova Biomedical, Waltham, Mass.) according the manufacturer's specifications. In addition to the sample media, medium from the 24 hour incubation was analyzed to ensure that none of the bones had been damaged during the collection process. Damaged bones release high levels of calcium into the medium and were not used in the final analyses. Results indicated that Zstc2 promotes bone resorption at a low level.

Example 5

The ability of Zstc2 to promote in mineralization by osteoblast cells was tested. Hamster Zstc2 was partially purified from a BHK cell line, as described above. The osteoblast cells were isolated from bone marrow of p53 deficient mice as progenitor cells. These cells can be induced to differentiate into osteoblasts, adipocytes, muscle cells or chrondocytes have been described in WO 96/07733, which is incorporated herein by reference. The cells were plated in 24 well plates (American Scientific Products, Chicago, Ill.).

Mineralization was induced by the addition of 10 mM b-glycerophosphate, 50 lg/ml ascorbic acid and 760 ng/ml Zstc2 to the culture medium. Culture medium contained α-MEM (JRH Biosciences, Lexena, Kans.), 1 mM sodium pyruvate (Irvine), 0.29 mg/ml L-glutamine, and 10% calf serum (Hyclone, Logan, Utah). Cells were grown in the supplemented medium and fresh medium containing Zstc2 was provided every 3–4 days and changes in morphology were identified microscopically. On the eighth day after plating, the medium was removed from the cells, and the wells were rinsed in PBS. Cells were fixed with Z-FIX (Anatech Ltd.). After fixing, the cells were rinsed three times with distilled water. A solution of five grams of silver nitrate in 100 ml of water was added to the cells at 1 ml/well and placed in the dark for 5 minutes. After incubation, the cells were rinsed three times in distilled water. A solution of 5 g of sodium carbonate, 75 ml distilled water and 25 ml of 38% formaldehyde was added to each well at 1 ml/well for 1 minute. The cells were rinsed 2–3 minutes with tap water. Farmer's Reducer (0.2 ml of 10% sodium thiosulphate, 1.0 ml of 0.1 g/ml potassium ferricyanide, 20 ml of water) was added at 1 ml/well for 1 minute. The cells were rinsed 10 minutes with tap water. Cells were scored visually for silver staining. Results demonstrated that at 4 days after the addition of stc2 mineralization was clearly visible for Zstc-2 treated cells, but was not seen in controls.

Calcium incorporation in the mineralized matrix was measured calorimetrically. Briefly, the medium was removed from the cells at day 5 after addition of Zstc-2 and the cells were rinsed in PBS. 300 µl of 0.5 M HCl was added to each well and the plates were incubated at room temperature overnight. Calcium quantitation was done using either using a calcium diagnostic kit (Sigma) which provided buffer and an agent to bind calcium producing a calorimetric change or a Nova 7/711 calcium analyzer (Waltham, Mass.), with protocols supplied by the manufacturer. A twenty-fold increase in calcium was seen in the Zstc-2 treated cells over the control cells.

Example 6

A.

The Stanniocalcin-2 gene was mapped to human chromosome 5 by PCR using the Human/Rodent Somatic Cell Hybrid Mapping Panel Number 2 (National Institute of General Medical Sciences, Coriell Institute of Medical Research, Camden, N.J.). The panel consisted of DNA isolated from 24 human/rodent somatic cell hybrids each retaining one specific human chromosome and the parental DNAs. Specific human stanniocalcin-2 oligonucleotide primers, designated ZC10,139 (SEQ ID NO: 8), agcggaggatccagcatgtttggtcaacg, and ZC10,140 (SEQ ID NO: 12), gtcatgcaaatcccatgtaagccccgaa, were used for PCR amplification. Each 50 µl PCR reaction consisted of 5 µl 10× KlenTaq PCR reaction buffer (Clontech Laboratories, Inc., Palo Alto, Calif.), 4 µl dNTPs mix (2.5 mM each, Perkin-Elmer, Norwalk, Conn.), 2.5 µl ZC10,139 (SEQ ID NO: 8) at 20 picomole/µl, 2.5 µl ZC10,140 (SEQ ID NO: 12) at 20 picomole/µl, 25 µl ddH2O, 1 µl 50× ADVANTAGE KlenTaq Polymerase Mix (Clontech Laboratories, Inc.), 10 µl DNA from the respective human/rodent somatic cell hybrid (10 ng/µl). PCR conditions were as follows: an initial 1 cycle for 10 minutes at 94° C.; 35 cycles for 1 minute at 94° C. and 90 second annealing at 68° C.; and a final 1 cycle extension of 7 minutes at 72° C. The reactions were separated by electrophoresis on a 30 NuSieve GTG agarose gel (FMC Bioproducts, Rockland, Me.). The results demonstrated that stanniocalcin-2 mapped to human chromosome 5.

B.

The human stanniocalcin-2 gene locus was mapped to the q arm of chromosome 5 using fluorescence in situ hybridization as follows:

I. Probe labeling with Bio-11-dUTP.

P1 clones designated 10978, 11043, 10977, and 11042 were prepared by screening high molecular weight libraries (GenomeSystems, Inc., St. Louis Mo.) with specific Zstc-2 oligonucleotide primers, ZC10,139 (SEQ ID NO: 8) and ZC10,140 (SEQ ID NO: 12). The P1 clones were used in the following reactions: 1 µg P1 clone DNA containing the human stanniocalcin-2 gene (GenomeSystems, Inc.), 5 µl 10× nick translation buffer (0.5 M Tris/HCl, 50 mM MgCl2, 0.5 mg/ml BSA (nuclease free), 5 µl dNTPs solution containing 0.5 mM DATP, 0.5 mM dGTP and 0.5 mM dCTP, 5 µl 5 mM Bio-11-dUTP, 5 µl 100 mM DTT, 5 µl DNase I (a 1000× dilution from a 10 U/µl stock, Boehringer Mannheim, RNase-free), 2.5 µl DNA polymerase I (5 U/µl, Boehringer Mannheim), and $dH_2O$ to a final volume of 50 µl. After mixing, the reactions were incubated at 15° C. for 1 hr. The reactions were stopped by adding 5 µl 0.5 M EDTA, pH 7.4 to the reaction. The biotin labeled P1 clones were purified using Worthington Biochemical Corporation G-50 DNA purification spins column according to the manufacture's instructions.

II. Slide preparation.

Metaphase chromosomes were obtained from a HEL cell culture. The culture was harvested as follows: 100 µl colcemid (GIBCO BRL, 10 µg/ml stock) was added to the medium of a 15 mm petri dish used for the cell culture and incubated at 37° C. for 2.5–3 hr. After incubation, the media was removed from the petri dish and transferred to a 15 ml "Blue Max" conical tube (Becton Dickinson, Cockeysville, Md.), 2 mls of 1×PBS (140 mM NaCl, 3 mM KCL, 8 mM $Na_2HPO_4$, 1.5 mM $KH_2PO_4$, pH 7.2) was added to the petri dish for rinsing and then 2 ml were added to the conical tube. 2 mls of trypsin (GIBCO BRL) was added to the petri dish, and the petri dish gently rocked and put into a 37° C. incubator for 3–5 min. The cells were then washed from the petri dish, and added to the tube with the media. The culture tube was centrifuged at 1100 rpm for 8 min. and all but 0.5 mls of the supernatant removed. The pellet was resuspended by tapping and then slowly and gently 8 mls of 0.075 M KCl (prewarmed to 37° C.) was added. The suspension was mixed gently and placed in a 37° C. water bath for 10 min. This was followed by a centrifugation at 1100 rpm for 5 min. and aspirating off all but 0.5 ml of the supernatant above the pellet. The pellet was resuspended by tapping the tube. Cold methanol:acetic acid (3:1) was added dropwise with shaking to fix the cells. 2 mls of fix were added in this manner. A total of 8 mls was added slowly and gently. The tube was placed at 4° C. for 20 min., followed by a 5 min. centrifugation at 1100 rpm. The supernatant was again aspirated off and the fixation process repeated two more times.

To drop metaphase spreads on 25×75 mm precleaned, frosted glass slides (VWR, Chester, Pa.), 5 µl of 50% acetic acid was spotted on each slide with a 20 µl Gilson Pipetman, followed by 5 µl of the cell suspension. The slides were allowed to air dry and then aged overnight in a 42° C. oven before use. The slides were scored for suitable metaphase spreads using a microscope equipped with a phase contrast condenser. Unused metaphase chromosome slide preparations were stored at −70° C.

III. Prehybridization and hybridization.

The hybridization mixes were made in the following manner (for each slide) In a 1.5 ml sterile Eppendorf tube, 2.5 ug competitor DNA (Cot-1 DNA, Gibco BRL), 60 ng biotin labeled P1 DNA containing the stanniocalcin-2 gene, 10 µg carrier DNA (denatured salmon testes DNA, Sigma), 1 µl 3 M NaOAc and 2 volumes ethanol were vacuum dried in a speedvac concentrator. The pellet was dissolved in 10 µl of a hybridization solution consisting of 10% dextran sulfate, 2×SSC and 50% formamide (EM Corp, Chestnut Hill, Mass.). The probe and competitor DNA were denatured at 70–80° C. for 5 min., chilled on ice and preannealed at 37° C. for 1–2 hr's. 10 ng of a denatured, biotinylated centromeric alpha satellite probe D1Z7/D5Z2/D19Z3 (Oncor, Gaithersburg, Md.) in hybridization solution was then added to the hybridization mix. Denaturation of the chromosomes was done by immersion of each slide in 70% formamide, 2×SSC at 70–80° C. for 5 min., followed by immediate cooling in ice-cold 70% ethanol and then 100% ethanol for 5–10 min. each. The slides were then air dried and warmed to 42° C. just before pipeting the hybridization mixtures onto them. The hybridization mixture and chromosomes were covered with a 18×18 mm, No 1 coverslip (VWR). The hybridizations proceeded in a moist chamber overnight at 37° C.

IV. Post-hybridization steps.

After removal of the coverslips, the slides were washed 3×5 min. in 50% formamide, 2×SSC at 42° C.; 3×5 min. in 2×SSC at 42° C.; and 1×3 min. in 4×SSC, 0.05% Tween-20 (polyoxyethylenesorbitan monolaurate, Sigma). This was followed by a 20 min. preincubation with 4×SSC containing 5% non-fat dry milk in a moist chamber (100 µl under a 24×50 mm coverslip). The posthybridization steps proceeded then with a 20 min. incubation with fluorescein avidin DCS (cell sorter grade, Vector, Burlingame, Calif.) (100 µl, 5 µg/ml, in 4×SSC, 5% non-fat dry milk under a 24×50 mm coverslip). The slides were then washed 3×3 min. in 4×SSC, 0.05% Tween-20, followed by a 20 min. incubation with biotiny-lated goat anti-avidin D (affinity purified, Vector) (5 µg/ml in 4×SSC, 5S non-fat dry milk under a 24×50 mm coverslip). The slides were washed again 3×3 min. in 4×SSC, 0.05% Tween 20, followed by another incubation with fluorescein avidin DCS (100 µl/ml in 4×SSC, 50 non-fat dry milk under a 24×50 mm coverslip). In some cases, the signal amplification procedure was repeated one additional time. The final washes were for 2×3 min. in 4×SSC, 0.05% Tween-20 and 1×3 min. in 1×PBS. The slides were mounted in antifade medium consisting of 9 parts glycerol containing 2% 1,4-diazobicyclo-(2,2,2)-octane (DABCO, dissolved at 70° C.) and one part 0.2 M Tris/HCl, pH 7.5 and 0.25–0.5 µg/ml propidium iodide. The slides were viewed on an Olympus BH2 microscope equipped with a BH2-RFC reflected light fluorescence attachment, a PM-10 ADS automatic photomicrographic system, an Optronics (Goleta, Calif.) ZVS-47E CCD RGB color video camera system and a Chroma Technology Corp. (Brattleboro, Vt.) FITC/Texas Red filter set for FITC visualization. Images of the metaphase chromosome spreads were digitized and stored using the Optronics video imaging camera system and Optimus software (Bothel, Wash.).

Example 7

A.

Scanning a cDNA database derived from a murine osteoblastic cell line revealed an EST which aligned with human stc2 from amino acid residue 192 (Gln) to residue 278 (Glu) of SEQ ID NO: 2 and included a gap of six amino acids in the mouse sequence as shown in FIG. 1.

B.

The cell line for constructing the cDNA library was isolated from calvaria of p53 knockout mice. Three p53 knockout mice (Taconic Farms, Germantown, N.Y.), approximately five weeks old, were sacrificed by cervical dislocation and swabbed with ethanol. The skin was removed from the animals and the femurs dissected out. In a sterile environment, the soft tissue was removed from the bone and the cortical ends cut off, leaving the long bone portion of the femur. Bone marrow was removed from the femur long bone by forcefully expressing the marrow from the medullary cavity using a 26 gauge needle and 10 cc syringe.

TABLE 5

500 ml a-MEM (GIBCO BRL, Gaithersburg, MD)
10% fetal calf serum (HyClone, Logan, Utah)
1 mM sodium pyruvate (Irvine, Santa Ana, CA.)
0.29 mg/ml L-glutamine (Hazelton, Lenexa,KS.)

The calvaria were placed in a 10 cc petri dish with 5 to 10 mls of growth medium (Table 5) containing 15% fetal calf serum. The calvaria were rinsed once in growth media. After rinsing, calvaria were placed in a Falcon centrifuge tube (Becton Dickinson Labware, Lincoln Park, N.J.) and minced using scissors. The minced bone was spun in a Beckman TJ-6 centrifuge (Beckman Instruments) at 1000 rpm for 10 minutes at room temperature. The bone was separated from the supernatant, and 3 ml of growth medium with 0.1% Type II collagenase (Sigma) was added to the minced bone pieces. The bone and collagenase mixture was incubated by shaking for 10 minutes at 37° C. After incubation, the supernatant was removed with a pipette, leaving bone pieces behind. The supernatant was placed in a 15 ml conical bottom Falcon centrifuge tube (Becton Dickinson Labware), and 3 ml of fetal calf serum was added to stop the collagenase digestion. The mixture was centrifuged at 1000 rpm for 10 minutes. After centrifugation, the cells were resuspended in 3 ml of growth medium with 15% fetal calf serum added to the medium. The collagenase digestion of the calvarial bone pieces was repeated five times, separating the supernatant from the bone pieces after each digestion. The bone pieces were washed five times in 15 ml of phosphate buffered saline (PBS) with 0.133 g/l calcium chloride-2H$_2$O and 0.1 g/l magnesium chloride-6 H$_2$O and then placed in growth medium with 15% fetal calf serum. Cultures containing cells from the serial digestions and bone pieces were placed at 37° C. and 50% CO$_2$ in growth medium. The cells were seen to crawl from the bone pieces after approximately 2–4 days.

The cells were replated at a clonal density of 1 cell/well in a 96-well petri dish containing growth medium. Single colonies were replica plated, with one replicate petri dish of the colony maintained as a cell line and the other used for characterization. The cells were positive for osteoblastic phenotype, demonstrated by testing for the presence of alkaline phosphatase, Von Kossa staining (to visualize mineralization, both in vivo and in vitro.

C.

Polyadenylated mRNA was isolated from the osteoblastic cells using Oligo-dT beads (Dynal, Olso, Norway), according to the manufacturer's specifications.

The first strand cDNA reaction contained 10 μl of mouse osteoblastic cell poly d(T)-selected poly (A)$^+$ mRNA at a concentration of 1.0 μg/μl, and 2 μl of 20 pmole/μl first strand primer ZC6172 (SEQ ID NO: 15) containing an Xho I restriction site. The mixture was heated at 65° C. for 3 minutes and cooled by chilling on ice. First strand cDNA synthesis was initiated by the addition of 8 μl of first strand buffer (5× SUPERSCRIPT™ buffer; Life Technologies, Gaithersburg, Md.), 4 μl of 100 mM dithiothreitol, and 2 μl of a deoxynucleotide triphosphate solution containing 10 mM each of DATP, dGTP and 5-methyl-dCTP (Pharmacia LKB Biotechnology, Piscataway, N.J.) to the RNA-primer mixture. The reaction mixture was incubated at 45° C. for 2 minutes, followed by the addition of 10 μl of 200 U/μl RNase H- reverse transcriptase (SUPERSCRIPT II®; Life Technologies). The efficiency of the first strand synthesis was analyzed in a parallel reaction by the addition of 10 μCi of $^{32}$P-α dCTP to 5 μl aliquot from one of the reaction mixtures to label the reaction for analysis. The reactions were incubated at 45° C. for 50 minutes, followed by an 4 incubation at 50° C. for 10 minutes. Unincorporated $^{32}$P-α dCTP in the labeled reaction was removed by chromatography on a 400 pore size gel filtration column (Clontech). The unicorporated nucleotides and primers in the unlabeled first strand reations were removed by chromatography on 400 pore size gel filtration column (Clontech). The length of labeled first strand cDNA was determined by agarose gel electrophoresis.

Second strand synthesis was performed on the RNA-DNA hybrid from the first strand synthesis reaction under conditions that promoted first strand priming of second strand synthesis resulting in DNA hairpin formation. A reaction mixture was prepared containing 20.0 μl of 5× polymerase I buffer (100 mM Tris, pH 7.4, 500 mM KCl, 25 mM MgCl$_2$, 50 mM (NH4)$_2$SO$_4$), 1.0 μl of 100 mM dithiothreitol, 2.0 μl of a solution containing 10 mM of each deoxynucleotide triphosphate, 3.0 μl of β-NAD, 1.0 μl of 3 U/μl E.coli DNA ligase (New England Biolabs, Beverly, Mass.), 5.0 μl of 10 U/μl E. coli DNA polymerase I (GIBCO BRL) and 50.0 μl of the unlabeled first strand DNA. A parallel reaction in which a 10 μl aliquot of the second strand synthesis was labeled by the addition 10 μCi of $^{32}$P-αdCTP was used to monitor the efficiency of second strand synthesis. The reaction mixtures were incubated at room temperature for 5 minutes followed by the addition of 1.5 μl of 2 U/μl RNase H (GIBCO BRL) to each reaction mixture. The reactions were incubated at 15° C. for 2 hours followed by a 30 minute incubation at room temperature. The reactions were terminated by addition 1 μl of 0.5 M EDTA and was precipitated in the presence of ethanol and 0.3 M sodium acetate. The first strand DNA was resuspended in 100 μl of water.

The single-stranded DNA in the hairpin structure was cleaved using mung bean nuclease. The reaction mixture contained 20.0 μl of 10× Mung Bean Nuclease Buffer (Stratagene Cloning Systems, La Jolla, Calif.), 16.0 μl of 100 mM dithiothreitol, 52.0 μl water, 50.0 μl of the second strand cDNA and 2.0 μl of 80 units/μl of Mung Bean nuclease (Promega Corp., Madison, Wis.). The reaction was incubated at 37° C. for 30 minutes, and the reaction was terminated by the addition of 20.0 μl of 1M Tris-HCl, pH 8.0 followed by sequential phenol/chloroform and chloroform/isoamylalcohol extractions as described above. Following the extractions, the DNA was precipitated in ethanol and resuspended in 150 μl water.

The resuspended cDNA was blunt-ended with T4 DNA polymerase. The cDNA, which was resuspended in a volume of 140 μl of water, was mixed with 40.0 μl of 5× T4 DNA polymerase buffer (250 mM Tris-HCl, pH 8.0, 250 mM KCl, 25 mM MgCl$_2$), 2.0 μl of 100 mM dithiothreitol, 4.0 μl of a solution containing 10 mM of each deoxynucleotide triphosphate and 2.0 μl of 1 U/μl T4 DNA polymerase (Boehringer Mannheim). After an incubation at 15° C. for 30 minutes, the reaction was terminated by serial phenol/chloroform and chloroform/isoamylalcohol extractions as described above. The DNA was ethanol precipitated and resuspended in 5.0 μl of water.

The cDNA was purified by chromatography through a TE400 Spin Column (Clontech), and was precipitated with a 2.5 volume of ethanol in the presence of 0.3 M sodium acetate.

D.

EcoR I adapters (Pharmacia LKB Biotechnology, Piscataway, N.J.) were added to the cDNA prepared above to facilitate the cloning of the cDNA into a mammalian expression vector. A 5.0 μl aliquot of the cDNA and 650 pmole of the adapter (10.0 μl) were mixed with 3.0 μl 10× Promega ligase buffer (Promega), 3.0 μl 10 mM ATP, 2.0 μl water and 30 Weiss Units of Promega DNA ligase (2.0 μl; Promega). The reaction was incubated overnight at 8° C. The reaction was terminated by the addition of 1.0 μl of H Buffer (Boehringer Mannheim, Indianapolis, Ind.) followed by an incubation at 65° C. for 30 minutes. The cDNA was purified by chromatography through a TE400 Spin column (Clontech), the DNA pellet was washed with 70% ethanol and was air dried. The pellet was resuspended in 20.0 μl of 2.5 mM Tris-HCl pH 8.0 and 0.25 mM EDTA.

F.

To facilitate the directional cloning of the cDNA into an expression vector, the cDNA was digested with Xho I, resulting in a cDNA having a 5' EcoR I cohesive end and a 3' Xho I cohesive end. The Xho I restriction site at the 3' end of the cDNA had been previously introduced using the ZC6172 primer (SEQ ID NO: 15). Restriction enzyme digestion was carried out in a reaction mixture containing 20 μl of cDNA described above, 2.5 μl of 10× H Buffer (Boehringer Mannheim), 1.5 μl H$_2$O, and 1.0 μl of 40 U/μl Xho I (Boehringer Mannheim). Digestion was carried out at 37° C. for 45 minutes. The reaction was terminated by the addition of 0.5 μl 0.5 M EDTA.

The cDNA was heated to 65° C. for 5 minutes, cooled on ice and electrophoresed on a 0.8% low melt agarose gel. The contaminating adapters and cDNA below 0.5 Kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (200 µl) and 25 µl 10× β-agarose I buffer (New England Biolabs) was added to the tube, and the agarose was melted by heating to 65° C. for 15 minutes. Following equilbration of the sample to 45° C., 5.0 µl of 1 U/µl β-agarose I (New England Biolabs) was added, and the mixture was incubated for 60 minutes at 44° C. to digest the agarose. After incubation, 30 µl of 3 M Na acetate was added to the sample, and the mixture was incubated on ice for 15 minutes. The sample was centrifuged at 14,000×g for 15 minutes at room temperature to remove undigested agarose. The cDNA was ethanol precipitated, washed in 70% ethanol, air-dried and resuspended in 32 µl water for the kinase reaction to phosphorylate the ligated EcoR I adaptors.

Five microliters of 10× ligase buffer (Stratagene Cloning Systems) was added to the 32.0 µl cDNA solution described above, and the mixture was heated to 65° C. for 5 minutes. The mixture was cooled on ice, and 5.0 µl of 10 mM ATP and 3.0 µl of 10 U/µl T4 polynucleotide kinase (Stratagene Cloning Systems) were added. The reaction was incubated at 37° C. for 30 minutes and was terminated by heating to 65° C. for ten minutes followed by serial extraction with phenol/chloroform and chloroform. The phosphorylated cDNA was ethanol precipitated in the presence of 0.3 M sodium acetate, wased with 70' ethanol, air dried and resuspended in 25 µl of 5 mM Tris-HCl pH 8.0, 0.5 mM EDTA. The concentration of the phosphorylated cDNA was estimated to be approximately 40 ng/µl.

The resulting cDNA was cloned into the lambda phage vector kZap® II that was predigested with EcoR I and Xho I and dephosphorylated (Stratagene Cloning Systems, La Jolla, Calif.). Ligation of the cDNA to the λZap® II vector was carried out in a reaction mixture containing 1.0 µl of prepared vector, 1.0 µl of mouse osteoblast cDNA, 1.0 µl 10× Ligase Buffer (Promega), 1.0 µl of 10 mM ATP, 5 µl water, and 1.0 µl of T4 DNA Ligase at 15 units/ml (Promega). The ligation mixture was incubated at 5° C.–15° C. overnight in a temperature gradient. After incubation, the ligation mixture was packaged into phage using GIG-PACK® III GOLD packaging extract (Stratagene Cloning Systems) and the resulting library was titered according to the manufacturer's specifications.

G.

The mouse osteoblast λZap® II library was used to infect XLI Blue MRF' host cells (Stratagene Cloning Systems), and 800–1000 pfu were plated onto 31 150-mm NZY plates. The inoculated plates were incubated overnight at 37° C. Filter plaques lifts were made using HYBOND-N nylon membranes (Amersham, Arlington Heights, Ill.), according to the procedures provided by the manufacturer. The filters were processed by denaturation in solution containing 1.5 M NaCl and 0.5 M NaOH for 7 minutes at room temperature. The filters were blotted briefly on filter paper to remove excess denaturation solution, followed by neutralization for 5 minutes in 1 M Tris-HCl, pH 7.5, and 1.5 M NaCl. Phage DNA was fixed onto the filters with 1,200 gjoules of UV energy in a STRATALINKER® UV Crosslinker (Stratagene Cloning Systems). After fixing, the filters were prehybridized in hybridization solution (5×SSC, 5×Denhardt's solution, 0.2% SDS and 1 mM EDTA). Heat denatured, sheared salmon sperm DNA at a final concentration of 100 µg/ml was added. The filters were prehybridized at 65° C. overnight.

Oligonucleotide ZC12453 (SEQ ID NO: 16) was labeled with $^{32}$P γATP in a reaction containing 12 µl of ZC12453 (SEQ ID NO: 16; 60 pmole), 8 µl water, 4 µl Promega 10× Ligase Buffer (Promega), 12 µl $^{32}$P γATP (150 Ci/ml; (Amersham, Arlington Heights, Ill.) and 4 µl of 10 U/ml T4 polynucleotide kinase (GIBCO-BRL, Gaithersburg, Md.). The reaction was incubated at 37° C. for 1 hour. The labeled product was purified on a NUC TRAP column (Stratagene).

The prehybridization solution was replaced with fresh hybridization solution containing 3.3×10$^5$ cpm/ml labeled probe and allowed to hybridize for overnight at 60° C. After hybridization, the hybridization solution was removed and the filters were rinsed in a wash solution containing 0.25× SSC, 0.25% SDS and 1 mM EDTA at 60° C. The filters were placed on autoradiograph film and exposed at −70° C. with intensifying screens for 96 hours.

Examination of the autoradiographs revealed 188 regions that hybridized with the labeled probe. Agar plugs were picked from 31 regions for purification. Each agar plug was soaked overnight in 1 ml of SM containing 1% (v/v) chloroform (Sambrook et al. *Molecular Cloning: A Laboratory Manual*, 2nd ed., Cold Spring Harbor Laboratory Press, Cold Spring Harbor, N.Y., 1989). After incubation, the phage from each plug were diluted 1:1000 in SM. Aliquots of 12.5 µl were plated on *E. coli* XL-1 Blue MRF' cells. The plates were incubated overnight at 37° C., and filter lifts were prepared, prehybridized, hybridized, washed and autoradiographed as described above. Examination of the resulting autoradiographs revealed positive signal on 1 filter lift.

The plasmids were excised using an ExASSIST/SOLR™ system (Stratagene Cloning Systems), according to the manufacturer's specification. These plasmids were amplified by PCR for size determination and sequencing. A clone, designated pSLMSTAN2–1, was shown to be 1846 bp and contained the sequence shown in SEQ ID NO: 13.

Example 8

In situ hybridization revealed that Zstc-2 was localized to pancreatic islet cells.

Briefly, antisense and sense riboprobes to human Zstc-2 were generated by PCR. The PCR primers contained sequences for T3 and T7 bacteriophage promoters and were designed to generate a probe corresponding to nucleotide 295 to nucleotide 549 of SEQ ID NO: 1. Sense and antisense riboprobes were generated by in vitro transcription from the PCR templates and labeled with $^{32}$P UTP of greater than 2,000 Ci/mmol (Amersham, Arlington Heights, Ill.).

In preparation for hybridization, sections tissues were treated sequentially with 4% paraformaldehyde for 10 minutes and proteinase K (0.5 µg/ml) for 15 minutes and then prehybridized with o50 µl of hybridization buffer (10% dextran sulfate, 2×SSC and 50% foramide) for 2 hours at 42° C. Probes were added at a final concentration of 10$^6$ cpm/slide, and incubated overnight at 55° C. Post-hybridization washes consisted of 2×SSC with 1 mm EDTA before and after a 30 minute treatment with ribonuclease (20 µg/ml). A high-stringency wash consisting of 0.1×SSC and EDTA was performed in a large volume for 2 hours at 55° C. Sections were then washed in 2×SSC, dehydrated in increasing concentration of ethanol and vacuum desiccated. Slides were coated with NTB2 nuclear emulsion (Eastman Kodak, Rochester, N.Y.) and exposed for up to 5 weeks. After development, the slides were counterstained with hematoxylin and eosin, and evaluated by dark field microscopy. Serial sections of tissue hybridized with the sense probes served as negative controls. Results the in situ hybridization demonstrated that stc2 is found in pancreas.

Example 9

Expression of stc2 was examined in normal and tumor tissues. Tissues that were analyzed included samples from normalGRID™ and TumorGRID™ multi-tissue control slides (Biomeda, Foster City, Calif.), normal human pancreas, human heart and human skeletal muscle (IIAM, Exton, Pa.). Stc2 transfected CHO cells and untransfected CHO cells were used as positive and negative controls, respectively. All tissues were fixed in 10% NBF (neutral buffered formalin) overnight and paraffin embedded. Immunostaining was carried out using a TechMate 500 autoimmunstainer (Biotech/Ventana) using the MIP protocol, according to the manufacturer's directions. Serial dilutions of the primary antibody (D3656, Rabbit anti-B129 factor "x" pool A, 0.47 mg/ml) were made in ChemMate primary antibody dilution buffer (CMS/Fisher, Seattle, Wash.). As a control, primary antibody was preabsorbed with sct-2 peptide (3.5 μg D3656, 6.0 μg 2× B219-factor "x" peptide, in antibody dilution buffer). Briefly, the immunostaining procedure involved removal of paraffin from the slides with xylene, followed by EtOH and a water wash. The slides were then pretreated with heat induced epitope retrieval for 20 minutes (HIER procedure, ChemMate, CMS/Fisher). The slides were then blocked with goat blocking antibodies (ChemMate, CMS/Fisher). The slides were then incubated with either the diluted (1:100, 1:200 or 1:400) primary antibody, preabsorbed primary antibody, or antibody dilution buffer only, followed by a wash in WASHING BUFFER (ChemMate, CMS/Fisher). Secondary antibody (biotinylated goat anti-rabbit, CMS/Fisher) was then added followed by a wash WASHING BUFFER 2 (ChemMate, CMS/Fisher). The slides were then incubated with ABC (avidin/biotin complex) followed by DAB (3,3'-diaminobenzidine peroxidase substrate) (ChemMate peroxidase/DAB staining kit, CMS/Fisher) prepared according to manufacturer's instructions. The slides were counterstained with Hematoxylin (ChemMate, CMS/Fisher) and cleared with EtOH and xylene, mounted and visualized. Staining was strongest in human pancreas a cells and intercalated discs marking the intercellular boundaries in the myocarium in the heart. No staining was detected on slides which were treated with preabsorbed antibody or received no primary antibody.

Example 10

A.

The human PTH receptor cDNA was expressed in a BHK570 cell line (ATCC accession no.10314) stably transfected with pKZ10, an expression unit comprising a promoter containing two cyclic AMP response elements, the luciferase cDNA and the hGH terminator. This cell line permits the measurement of CRE-regulated luciferase activity, which is an indirect measurement of elevated cAMP levels.

The enkephalin cyclic AMP response element (CRE) in plasmid ZK6 was obtained from Zem233. Zem233 was derived from plasmids Zem67 and Zem106. Plasmid Zem106 was constructed from the precursor Zem93. To construct Zem93, a Kpn I-BamH I fragment comprising the MR-1 promoter was isolated from MThGH111 (Palmiter et al., *Science* 222:809–814, 1983) and inserted into pUC18. Plasmid Zem93 was then digested with Sst I and re-ligated to generate plasmid Zem106, in which approximately 600 bp of sequence 5' to the MT-1 promoter were eliminated.

An enkephalin CRE was inserted into Zem106 by first digesting Zem106 with EcoR I and Sst I to isolate the vector-containing fragment. Oligonucleotides ZC982 and ZC983 (Sequence ID Nos. 17 and 18, respectively) were designed to encode when annealed a proenkephalin CRE from nucleotides −71 to −133 (Comb et al., *Nature* 323: 353–356, 1986) flanked by a 5' EcoR I site and a 3' Sst I site. Oligonucleotides ZC982 and ZC983 (Sequence ID Nos. 17 and 18, respectively) were kinased, annealed and ligated with the linearized Zem106 to obtain plasmid Zem224.

Plasmid Zem67 was obtained by first digesting pICI9R (Marsh et al., *Gene* 32: 481–486, 1984) with Sma I and Hind III. The ori region of SV40 from map position 270 (Pvu II) to position 5171 (Hind III) was then ligated to the linearized pICI9R to produce plasmid Zem67. The Hind III-BamH I neomycin resistance gene-SV40 terminator fragment from plasmid pSV2-neo (available from ATCC as Accession no. 37149) was inserted into Hind III-Bgl II digested Zem67 to obtain Zem220.

The SV40 promoter-neomycin resistance gene-SV40 terminator expression unit from plasmid Zem220 was isolated as an EcoR I fragment. Plasmid Zem224 was digested with EcoR I and treated with calf alkaline phosphatase to prevent recircularization. The neomycin expression unit and the linearized Zem224 were ligated. A plasmid containing the SV40 promoter proximal to the CRE was designated Zem233.

Plasmid Zem233 was modified to insert an additional CRE sequence, a TATA box, and a portion of the lacZ coding and poly(A) sequences immediately 3' to the proenkephalin CRE sequence such that the resulting expression unit was in the opposite orientation relative to the neomycin resistance expression unit present in Zem233. Plasmid Zem233 was linearized by digestion with Sst I and BamH I. Oligonucleotides ZC3509 and ZC3510 (Sequence ID Nos. 19 and 20, respectively) were designed such that when annealed, the resulting duplex encodes a glycoprotein CRE (Delegeane et al., *Mol. Cell. Biol.* 7: 3994–4002, 1987) with a 5' Sst I adhesive end and a 3' EcoR I adhesive end. The oligonucleotides were annealed according to standard procedures. The thymidine kinase TATA box was obtained as an EcoR I-Pst I fragment spanning nucleotides −79 to +18 of the thymidine kinase gene (McKnight, *Cell*: 355–366, 1982). The 3' sequence of the lacZ gene and its associated poly(A) sequence were obtained as a Pst I-BamH I fragment from plasmid pLacF (obtained from Jacques Peschon, Immunex Corp., Seattle, Wash.), which contains the lacZ coding region and mouse protamine terminator sequence cloned into the pUC18 vector. The Sst I-BamH I linearized Zem233, the Sst I-EcoR I ZC3509/ZC3510 adapter, the EcoR I-Pst I TATA box fragment and the Pst I-BamH I lacZ sequence were ligated. A plasmid containing the expression unit in the correct orientation relative to the neomycin resistance gene expression unit of Zem233 was designated KZ5.

The luciferase gene and human growth hormone (hGH) terminator sequences were used to replace the lacZ coding and poly(A) sequences present in KZ5. The luciferase gene was initially obtained from plasmid a-1681uc (Delegeane et al., *Mol. Cell. Biol.*7: 3994–4002, 1987 and dewet et al., *Mol. Cell. Biol.*7: 725–737, 1987) as a 1.7 kb Xho I-Xba I fragment. The hGH terminator was obtained as an Xba I-Sal I fragment from Zem219b (deposited as an *E.coli.* transformant with the ATCC under Accession no. 6879). The luciferase gene and hGH terminator sequences were subcloned into Xho I-Sal I linearized pIC19H (Marsh et al., ibid.) for convenience. The resulting plasmid, KZ8, was digested with Xho I and Sal I to isolate the luciferase-hGH terminator sequences. Plasmid KZ5 was digested with Sal I to isolate the vector-containing fragment and was treated with calf alkaline phosphatase to prevent recircularization. The Xho I-Sal I luciferase-hGH terminator fragment was ligated with the Sal I-digested KZ5. A plasmid containing the luciferase-hGH terminator in the proper orientation relative to the promoter was designated KZ6.

Plasmid KZ6 was digested with Hind III to remove a DNA fragment containing the SV40 promoter, CRE unit, luciferase gene, human growth hormone gene and poly(A) sequences. Zem219b (ATCC Accession no. 68979) was digested with Hind III to isolate the DHFR gene and pUC18 sequences. The KZ6 and Zem219b DNA fragments were gel purified isolated as a 3.0 kb fragment and a 5.0 kb fragment, respectively, and ligated. The resulting plasmid containing a CRE-responsive luciferase gene and DHFR selectable marker was designated plasmid KZ10.

Plasmid KZ10 was transfected into BHK570 cells (available from ATCC as Accession no. CRL 10314) using the calcium phosphate precipitation method essentially as described by Graham and Van de Eb (*Virol*.52: 456, 1973, which is incorporated by reference herein). The transfected cells were grown in growth medium (Dulbecco's modified Eagle's medium (DMEM) containing 10% fetal calf serum and 2.0 mM L-glutamine). After a few days in non-selective growth medium, the growth medium was replaced with methotrexate (MTX) selection medium (growth medium containing 250 nM MTX). The cells were then allowed to grow to confluence after which they were trypsinized and plated as limiting dilution into the wells of 96-well plates. The cells were grown for one to two weeks in methotrexate selection medium. Clones from wells containing single colonies were assayed for the ability to respond to forskolin in the luciferase assay described below. Forskolin elevates the cellular cAMP level and thus the associated cAMP-dependent biological response pathways in a receptor-independent manner. A clone capable of responding to forskolin was designated BHK/KZ10-20-48.

The same pKZ10 construct, e.g., the CRE-construct, was transfected into CCC4 cells, a mature osteoblast cell line derived from p53-/- (deficient) mice. These cells express endogenous PTH receptors.
B.

Receptor-positive and -negative BHK transfectants were maintained by serial passage in growth medium (DMEM supplemented with 10% HI-FBS, 2 mM L-glutamine, 1 mM sodium pyruvate, 250 nM MTX, and 1 mg/ml G418). On the day prior to assay, cells were trypsynized, adjusted to $2 \times 10^5$ cells/ml in growth medium, plated in opaque white Dynatech Microlite microtiter tissue culture plates at 100 $\mu$l/well ($2 \times 10^4$ cells), and grown overnight to confluence, at 37° C., in 5% $CO_2$. Transfected CCC4 cells were maintained in αMEM, 20% fetal calf serum, 2 mM glutamine and 1 mM sodium pyruvate.

PTH and human or hamster stanniocalcin-2 were dissolved in medium without serum, at 100 times the final desired assay concentration. Induction was initiated by removing spent medium from the wells and adding 100 $\mu$l/well test substance diluted 1:100 (final concentration ranging from 20–1000 ng/ml in DMEM or aMEM supplemented with 10% HI-FBS, 2 mM L-glutamine, 1 mM sodium pyruvate and 10 mM Hepes, pH 7.25). Controls were included on each plate: untreated wells (basal), 25 mM forskolin, and 100 nM human PTH. Plates were incubated for 3 to 8 hours (4 hours preferred) at 37° C., in 5% $CO_2$.

Following induction, luciferase activity was measured using a Promega luciferase assay kit (E1500, Promega Corp., Madison, Wis.) according to the assay kit protocol. The plates were transferred to a Labsystems Lumiscan microtiter luminometer which added 40 $\mu$l/well Luciferase Assay Substrate (Promega Corp.). The amount of luminescence (relative light units, RLU) was determined following a 1 second mix and a 1–3 second integration of signal. Basal (uninduced) luciferase signal was subtracted from all measurements, and the luciferase signal induced by test samples was expressed as a percentage of the signal in the PTH and forskolin controls.

Results clearly demonstrated that stc2 enhances a sub-maximal PTH-induced cAMP response in CCC4 mouse osteoblast cells but not in BHK cells transfected with the PTH receptor. Thus, osteoblast cells are target cells and the action of stc2 is receptor-mediated which utilizes cAMP as a second messenger, or indirectly modulates cAMP levels.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated stanniocalcin-2 polypeptide comprising a sequence of amino acids as shown in SEQ ID NO: 2 from amino acid residue 15 (Ser) to amino acid residue 184 (Leu).

2. The isolated stanniocalcin-2 polypeptide of claim 1, wherein the amino acid sequence is the sequence as shown in SEQ ID NO: 2 from amino acid residue 1 to residue 278.

3. The isolated stanniocalcin-2 polypeptide of claim 1, wherein the sequence comprises amino acid residues 1 to 278 as shown in SEQ ID NO: 2.

4. The isolated stanniocalcin-2 polypeptide of claim 1, wherein the sequence comprises amino acid residues −24 to 278 of SEQ ID NO: 2.

5. A pharmaceutical composition comprising purified stanniocalcin-2 according to claim 1, in combination with a pharmaceutically acceptable vehicle.

6. An isolated stanniocalcin-2 polypeptide comprising a sequence of amino acid residues as shown in SEQ ID NO: 14 from residue 1 to 272.

7. The isolated stanniocalcin-2 polypeptide of claim 1, wherein the amino acid sequence is the sequence as shown in SEQ ID NO: 14 from amino acid residue 1 to residue 272.

8. The isolated stanniocalcin-2 polypeptide of claim 6, wherein the sequence comprises amino acid residues −24 to 272 of SEQ ID NO: 14.

* * * * *

UNITED STATES PATENT AND TRADEMARK OFFICE
CERTIFICATE OF CORRECTION

PATENT NO : 6,008,322
DATED : Dec. 28, 1999
INVENTOR(S) : Rolf E. Kuestner, Darrell C. Conklin, Si Lok, Michele Buddle, William Downey It is certified that error appears in the above-identified patent and that said Letters Patent are hereby corrected as shown below:

On the cover page, please add the following:

--Related U.S. Application Data
Provisional application No. 60/015,137, Apr. 2, 1996. --

Signed and Sealed this

Tenth Day of April, 2001

Attest:

NICHOLAS P. GODICI

Attesting Officer

Acting Director of the United States Patent and Trademark Office